(12) United States Patent
Otake

(10) Patent No.: US 10,533,107 B2
(45) Date of Patent: *Jan. 14, 2020

(54) COMPOSITION SET, SHAPED ARTICLE PRODUCTION METHOD, AND SHAPED ARTICLE

(71) Applicant: SEIKO EPSON CORPORATION, Tokyo (JP)

(72) Inventor: Toshihiro Otake, Matsumoto (JP)

(73) Assignee: Seiko Epson Corporation, Tokyo (JP)

( * ) Notice: Subject to any disclaimer, the term of this patent is extended or adjusted under 35 U.S.C. 154(b) by 663 days.

This patent is subject to a terminal disclaimer.

(21) Appl. No.: 15/060,371

(22) Filed: Mar. 3, 2016

(65) Prior Publication Data

US 2016/0289481 A1 Oct. 6, 2016

(30) Foreign Application Priority Data

Mar. 30, 2015 (JP) .................................. 2015-068279

(51) Int. Cl.

| | | |
|---|---|---|
| G02F 1/1333 | (2006.01) | |
| C09D 101/10 | (2006.01) | |
| C08B 3/00 | (2006.01) | |
| A61L 31/04 | (2006.01) | |
| B33Y 10/00 | (2015.01) | |
| B33Y 70/00 | (2015.01) | |
| B33Y 80/00 | (2015.01) | |
| B29K 1/00 | (2006.01) | |
| B29K 105/00 | (2006.01) | |

(52) U.S. Cl.
CPC .......... *C09D 101/10* (2013.01); *A61L 31/042* (2013.01); *C08B 3/00* (2013.01); *B29K 2001/08* (2013.01); *B29K 2105/0002* (2013.01); *B29K 2105/0079* (2013.01); *B33Y 10/00* (2014.12); *B33Y 70/00* (2014.12); *B33Y 80/00* (2014.12)

(58) Field of Classification Search
CPC ......... A61L 34/042; C08B 3/00; B33Y 10/11; B33Y 70/00; B33Y 80/00; B29K 2001/08; B29K 2105/0002; B29K 2105/0079; G02F 1/1333; C09D 101/10
USPC .................................................. 252/299.01
See application file for complete search history.

(56) References Cited

U.S. PATENT DOCUMENTS

| | | |
|---|---|---|
| 5,549,861 A | 8/1996 | Huber et al. |
| 6,197,224 B1 | 3/2001 | Shinamoto |
| 7,141,617 B2 | 11/2006 | Gratson et al. |
| 7,163,723 B2 | 1/2007 | Tanaka et al. |
| 7,416,683 B2 | 8/2008 | Fujisawa et al. |
| 8,436,117 B2 | 5/2013 | Otake |
| 8,440,773 B2 | 5/2013 | Otake |
| 9,670,619 B2 | 6/2017 | Otake |
| 9,796,790 B2 | 10/2017 | Otake et al. |
| 10,174,184 B2 | 1/2019 | Otake et al. |
| 2004/0141121 A1 | 7/2004 | Tanaka et al. |
| 2006/0060821 A1 | 3/2006 | Fujisawa et al. |
| 2006/0235105 A1 | 10/2006 | Gratson et al. |
| 2007/0093655 A1 | 4/2007 | Oya |
| 2008/0173419 A1 | 7/2008 | Summicht |
| 2010/0274001 A1 | 10/2010 | Okutsu et al. |
| 2011/0196120 A1 | 8/2011 | Otake |
| 2012/0046431 A1 | 2/2012 | Otake |
| 2012/0101269 A1 | 4/2012 | Buchanan et al. |
| 2012/0122691 A1 | 5/2012 | Daly et al. |
| 2013/0209779 A1 | 8/2013 | Iida et al. |
| 2014/0162033 A1 | 6/2014 | Giller |
| 2014/0212670 A1 | 7/2014 | Shinamoto et al. |
| 2015/0148458 A1 | 5/2015 | Koide et al. |
| 2016/0145356 A1 | 5/2016 | King et al. |
| 2016/0145422 A1 | 5/2016 | Otake |
| 2016/0145455 A1 | 5/2016 | Otake |
| 2016/0280948 A1* | 9/2016 | Otake .................... C08B 3/00 |
| 2016/0289481 A1* | 10/2016 | Otake .................. C09D 11/10 |

FOREIGN PATENT DOCUMENTS

| | | |
|---|---|---|
| CN | 1732218 A | 2/2006 |
| CN | 103360619 | 10/2013 |
| EP | 1 396 738 | 3/2004 |
| JP | 45-020318 | 7/1970 |
| JP | 07-268724 | 10/1995 |
| JP | 09-296001 | 11/1997 |
| JP | 2000-147258 A | 5/2000 |
| JP | 2004-163452 A | 6/2004 |
| JP | 2005-076026 | 3/2005 |
| JP | 2007051241 | 3/2007 |
| JP | 2007-308616 | 11/2007 |

(Continued)

OTHER PUBLICATIONS

European Search Report for Application No. 16162313.7 dated Jul. 14, 2016.

(Continued)

*Primary Examiner* — Geraldina Visconti
(74) *Attorney, Agent, or Firm* — Workman Nydegger

(57) ABSTRACT

A composition set according to the invention includes a first composition which contains a cellulose derivative having a liquid crystalline functional group, and a second composition which contains a liquid crystalline compound having a reactive functional group and can be in a liquid state. The first composition preferably contains particles whose surfaces are at least partially constituted by the cellulose derivative. Further, the first composition preferably contains a liquid component which functions as a dispersion medium for dispersing the particles.

16 Claims, 4 Drawing Sheets

(56) References Cited

FOREIGN PATENT DOCUMENTS

| | | |
|---|---|---|
| JP | 2008-248217 | 10/2008 |
| JP | 2009-102587 | 5/2009 |
| JP | 2010-001397 | 1/2010 |
| JP | 2011-162447 | 8/2011 |
| JP | 2012-041282 | 3/2012 |
| JP | 2012-041405 | 3/2012 |
| JP | 2012-126755 | 7/2012 |
| JP | 2013-035251 | 2/2013 |
| JP | 2013-126268 | 6/2013 |
| JP | 2013-540629 | 11/2013 |
| JP | 2013-241702 | 12/2013 |
| JP | 2015-028039 | 2/2015 |
| JP | 2015-054876 | 3/2015 |
| JP | 2016-527330 | 9/2016 |
| WO | 2002093213 A | 11/2002 |
| WO | 03/029329 | 4/2003 |
| WO | 2012-058278 | 5/2012 |

OTHER PUBLICATIONS

European Search Report for Application No. 16162311.1 dated Jul. 14, 2016.

* cited by examiner

COMPOSITION SET, SHAPED ARTICLE PRODUCTION METHOD, AND SHAPED ARTICLE

CROSS-REFERENCE TO RELATED APPLICATIONS

This application claims priority to Japanese Patent Application No. 2015-068279 filed on Mar. 30, 2015. The entire disclosures of Japanese Patent Application No. 2015-068279 is hereby incorporated herein by reference.

BACKGROUND

1. Technical Field

The present invention relates to a composition set, a shaped article production method, and a shaped article.

2. Related Art

Cellulose is a recyclable resource and is accumulated abundantly on earth, and also has excellent biocompatibility and degradability, and therefore is an environmentally friendly material. Accordingly, cellulose has attracted attention recently, and its effective utilization has been demanded (see, for example, JP-A-7-268724).

However, in the past, cellulose was used in paper products such as printing paper and corrugated cardboard in most cases, and other than these, it was merely used in fibers (cellulose fibers) and the like. Therefore, there was a problem that various advantageous characteristics of cellulose are not fully utilized.

Further, cellulose has been known to be able to constitute a member having excellent mechanical strength because of its chemical structure, however, it has not yet been applied on a practical level to a member having high strength and high durability which sufficiently exhibits the characteristics of cellulose.

SUMMARY

An advantage of some aspects of the invention is to provide a composition set which can be favorably used for producing a shaped article which contains a cellulosic material and has excellent strength, to provide a shaped article which contains a cellulosic material and has excellent strength, and to provide a shaped article production method capable of efficiently producing a shaped article which contains a cellulosic material and has excellent strength.

The advantage can be achieved by the invention described below.

A composition set according to an aspect of the invention includes a first composition which contains a cellulose derivative having a liquid crystalline functional group, and a second composition which contains a liquid crystalline compound having a reactive functional group and can be in a liquid state.

According to this configuration, a composition set which can be favorably used for producing a shaped article which contains a cellulosic material and has excellent strength can be provided.

In the composition set according to the aspect of the invention, it is preferred that the first composition contains particles whose surfaces are at least partially constituted by the cellulose derivative.

According to this configuration, a shaped article having stable quality and properties can be produced more stably and more efficiently.

In the composition set according to the aspect of the invention, it is preferred that the first composition contains a liquid component which functions as a dispersion medium for dispersing the particles.

According to this configuration, the productivity of the shaped article can be made more excellent. Further, in the case where the first composition contains particles, undesirable scattering or the like of the particles when producing the shaped article can be effectively prevented.

In the composition set according to the aspect of the invention, it is preferred that the particles have an average particle diameter of 1 μm or more and 25 μm or less.

According to this configuration, the mechanical strength of the shaped article can be made more excellent, and also the dimensional accuracy of the shaped article can be made more excellent. Further, the productivity of the shaped article can be made more excellent.

In the composition set according to the aspect of the invention, it is preferred that the second composition does not contain a liquid component other than the liquid crystalline compound.

According to this configuration, the productivity of the shaped article can be made more excellent. Further, the dimensional accuracy of the shaped article can be made more excellent.

In the composition set according to the aspect of the invention, it is preferred that the reactive functional group contains a carbon-carbon double bond.

According to this configuration, the productivity of the shaped article can be made more excellent. Further, the strength, durability, and reliability of the shaped article can be made more excellent.

In the composition set according to the aspect of the invention, it is preferred that the reactive functional group is a (meth)acryloyl group.

According to this configuration, the productivity of the shaped article can be made furthermore excellent. Further, the strength, durability, and reliability of the shaped article can be made further more excellent.

In the composition set according to the aspect of the invention, it is preferred that the cellulose derivative has the liquid crystalline functional group introduced into a repeating unit of a polymer chain having a repeating structure introduced into a cellulose backbone structure.

According to this configuration, the mechanical strength, durability, and reliability of the shaped article can be made more excellent.

In the composition set according to the aspect of the invention, it is preferred that a chemical reaction involving the reactive functional group of the liquid crystalline compound proceeds by UV irradiation.

According to this configuration, the productivity of the shaped article can be made more excellent while more effectively preventing undesirable denaturation, deterioration, or the like of the materials. Further, the structure of a production apparatus for the shaped article can be prevented from being complicated, and thus, the production cost of the shaped article can be kept low.

A shaped article production method according to an aspect of the invention includes producing a shaped article using the composition set according to the aspect of the invention.

According to this configuration, a shaped article production method capable of efficiently producing a shaped article which contains a cellulosic material and has excellent strength can be provided.

A shaped article production method according to an aspect of the invention includes bringing a first composition which contains a cellulose derivative having a liquid crystalline functional group and a second composition which is in a liquid state and contains a liquid crystalline compound having a reactive functional group into contact with each other, and allowing a chemical reaction involving the reactive functional group of the liquid crystalline compound to proceed.

According to this configuration, a shaped article production method capable of efficiently producing a shaped article which contains a cellulosic material and has excellent strength can be provided.

A shaped article production method according to an aspect of the invention is a method for producing a three-dimensional shaped article by performing a layer forming step of forming a layer a plurality of times and stacking the layers, and includes applying a first composition which contains a cellulose derivative having a liquid crystalline functional group and a second composition which is in a liquid state and contains a liquid crystalline compound having a reactive functional group to a region where the three-dimensional shaped article is to be formed so that the first composition and the second composition come in contact with each other, and allowing a chemical reaction involving the reactive functional group of the liquid crystalline compound to proceed.

According to this configuration, a shaped article production method capable of efficiently producing a shaped article which contains a cellulosic material and has excellent strength can be provided. Further, even a shaped article required to have high dimensional accuracy or a shaped article having a complicated shape can be efficiently produced with sufficient dimensional accuracy. Further, the production method can be favorably applied also to the production of a plurality of types of shaped articles having different shapes and sizes.

A shaped article production method according to an aspect of the invention is a method for producing a three-dimensional shaped article by stacking layers, and includes a layer forming step of forming the layer using a first composition which contains a plurality of particles constituted by a material containing a cellulose derivative having a liquid crystalline functional group, a second composition application step of applying a second composition which is in a liquid state and contains a liquid crystalline compound having a reactive functional group to the layer, and a solidification step of solidifying the second composition by allowing a chemical reaction involving the reactive functional group of the liquid crystalline compound to proceed.

According to this configuration, a shaped article production method capable of efficiently producing a shaped article which contains a cellulosic material and has excellent strength can be provided. Further, even a shaped article required to have high dimensional accuracy or a shaped article having a complicated shape can be efficiently produced with sufficient dimensional accuracy. Further, the production method can be favorably applied also to the production of a plurality of types of shaped articles having different shapes and sizes.

In the shaped article production method according to the aspect of the invention, it is preferred that the application of the second composition is performed by an inkjet method.

According to this configuration, the dimensional accuracy of the shaped article can be further increased.

In the shaped article production method according to the aspect of the invention, it is preferred that the first composition and the second composition are applied onto a member having been subjected to an alignment treatment.

According to this configuration, the mechanical strength, durability, reliability, and the like of the shaped article to be obtained finally can be made more excellent.

A shaped article according to an aspect of the invention is produced using the composition set according to the aspect of the invention.

According to this configuration, a shaped article which contains a cellulosic material and has excellent strength can be provided.

A shaped article according to an aspect of the invention is produced using the production method according to the aspect of the invention.

According to this configuration, a shaped article which contains a cellulosic material and has excellent strength can be provided.

It is preferred that the shaped article according to the aspect of the invention is a stent.

A stent is held in a state of being inserted into the body for a long period of time, and is required to have excellent strength, durability, biocompatibility, and the like. However, according to the invention, these requirements can be satisfied. Accordingly, when the invention is applied to a stent, the effect of the invention can be more remarkably exhibited.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1A:
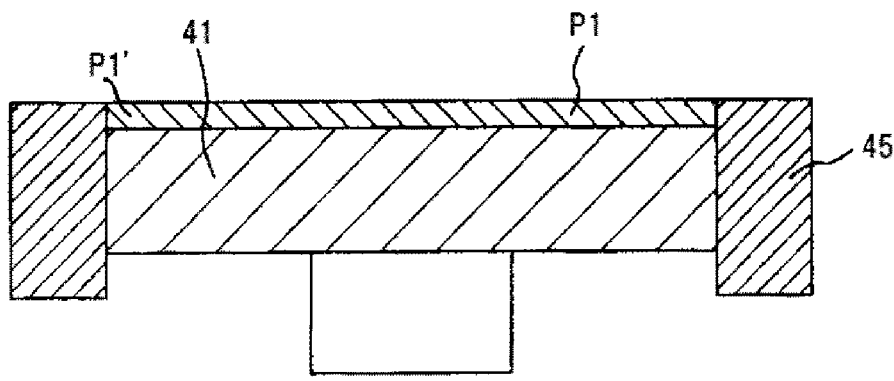
FIGS. 1A to 1H show cross-sectional views schematically illustrating respective steps in a preferred embodiment of a shaped article production method according to the invention.

Hereinafter, preferred embodiments of the invention will be described in detail with reference to the accompanying drawings.

Composition Set

First, a composition set according to the invention will be described in detail.

The composition set according to the invention is used for producing a shaped article, and includes a first composition which contains a cellulose derivative having a liquid crystalline functional group and a second composition which contains a liquid crystalline compound having a reactive functional group and can be in a liquid state.

According to this, a member (shaped article) to be produced using the composition set can be made to have excellent strength and the like while having the advantageous characteristics of cellulose.

More specifically, since both of the cellulose derivative and the liquid crystalline compound have a liquid crystalline moiety, the constituent materials can be favorably aligned in a shaped article to be produced using the composition set. According to this, the intermolecular interaction (intermolecular force) or the like of the constituent materials in the shaped article can be increased. Then, by allowing a chemical reaction involving the reactive functional group of the liquid crystalline compound to proceed in this state, the liquid crystalline compound is solidified (cured) in a state where the moiety having liquid crystallinity is aligned. Accordingly, the mechanical strength, durability, reliability, and the like of the shaped article to be obtained can be made excellent.

Hereinafter, the first composition and the second composition included in the composition set according to the invention will be described.

First Composition

The first composition contains a cellulose derivative having a liquid crystalline functional group.

Cellulose Derivative

Cellulose is a compound in which β-glucose is polymerized through a glycoside bond, however, in the invention, the cellulose derivative may be any as long as it is a compound which can be derived from cellulose by a chemical reaction, and examples thereof include a cellulose derivative obtained by substituting at least part of the hydroxy groups of cellulose with another substituent (including a cellulose derivative obtained by a condensation reaction of at least part of the hydroxy groups of cellulose with another compound, etc.).

The substituent may be introduced into all the repeating units (glucose structures) in the same manner, or may be introduced into only part of the repeating units (glucose structures). Further, the position where the substituent is introduced may be different among the repeating units (glucose structures).

The cellulose derivative contained in the first composition constituting the composition set according to the invention may be any as long as it has a functional group having liquid crystallinity (liquid crystalline functional group).

Examples of the functional group (atomic group) having liquid crystallinity include groups represented by the following formulae (6).

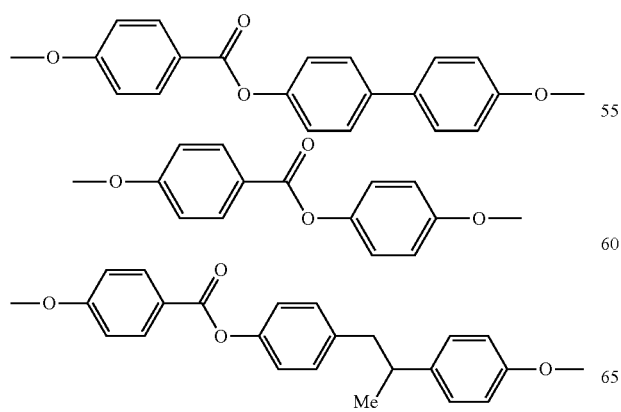

(6)

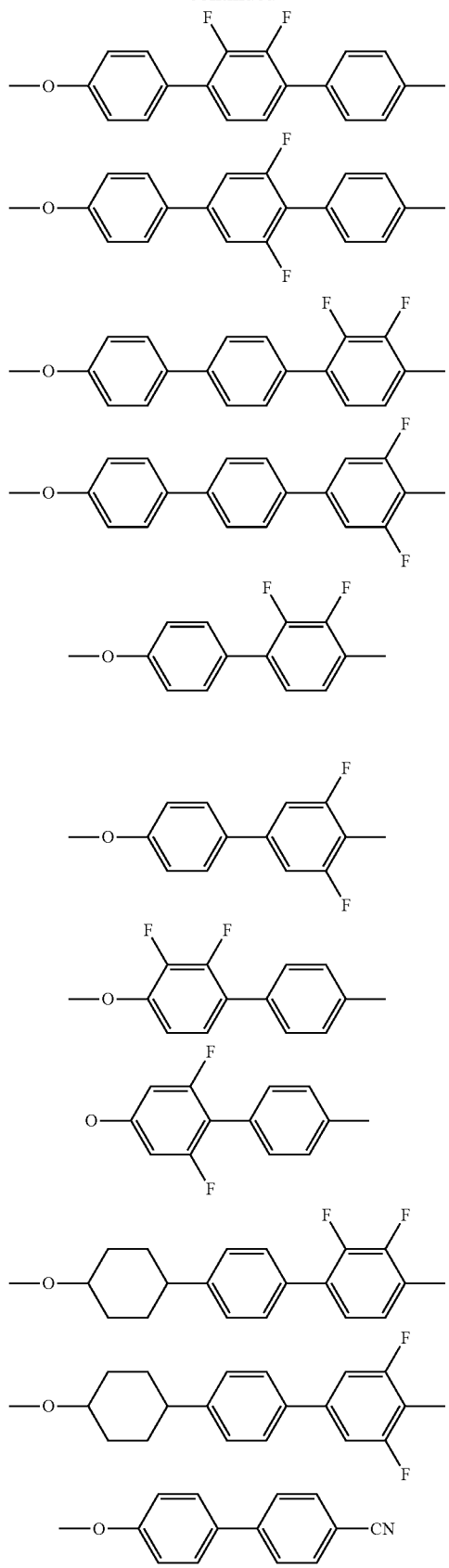

The liquid crystalline functional group may be introduced into any position of the cellulose derivative, but is preferably introduced into a hydroxy group bonded to the carbon atom at position 6 of β-glucose constituting cellulose by a chemical reaction. That is, it is preferred that the liquid crystalline functional group is introduced into $R^3$ in the following formula (2).

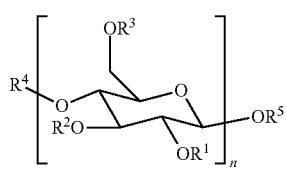

(2)

In the formula (2), $R^1$, $R^2$, $R^3$, $R^4$, and $R^5$ each independently represent a hydrogen atom or a substituent, provided that at least one functional group is introduced into the molecule.

According to this, the effect of the liquid crystalline functional group on the alignment of the cellulose derivative can be more remarkably exhibited, and thus, the strength, durability, and reliability of the shaped article can be made more excellent. Further, the synthesis of the cellulose derivative as the constituent component of the first composition can be efficiently performed. As a result, this configuration can also contribute to the reduction of the production cost of the shaped article.

At least one liquid crystalline functional group may be introduced into the molecule of the cellulose derivative, however, it is preferred that a plurality of liquid crystalline functional groups are introduced into the molecule of the cellulose derivative.

According to this, the cellulose derivatives can be more favorably arranged in the shaped article, and thus, the mechanical strength, durability, and reliability of the shaped article can be made more excellent.

In particular, it is preferred that a plurality of liquid crystalline functional groups are introduced into a repeating unit of a polymer chain (side chain) having a repeating structure introduced into a cellulose backbone structure (basic structure).

According to this, for example, in the cellulose derivative molecule, the liquid crystalline functional groups can be more reliably made to be regularly present. Further, the conditions for a plurality of liquid crystalline functional groups of the cellulose derivative molecule can be favorably aligned. As a result, the cellulose derivative can be made to be present at a high density in the shaped article, and thus, the mechanical strength, durability, and reliability of the shaped article can be made more excellent.

Specific examples of a preferred cellulose derivative satisfying such conditions include cellulose derivatives represented by the following formulae (7) and (8).

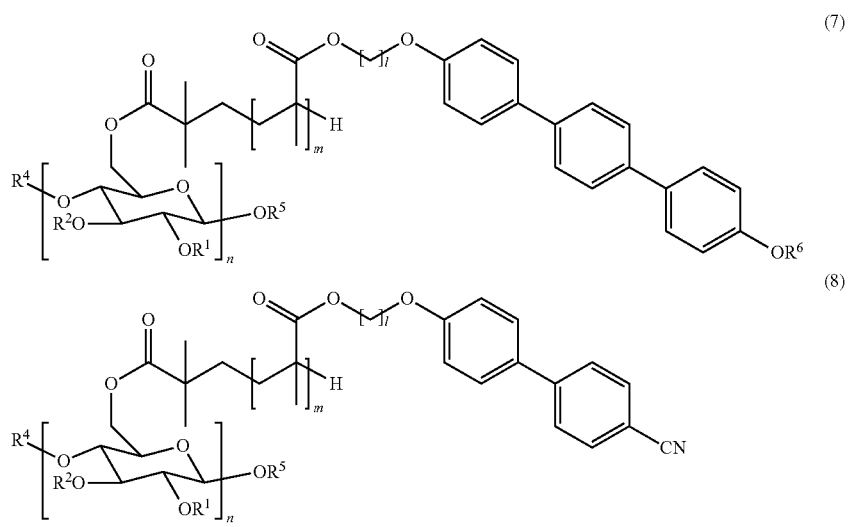

In the formulae (7) and (8), n is an integer of 2 or more, l and m are each independently an integer of 1 or more, $R^1$, $R^2$, $R^4$, and $R^5$ are each independently a hydrogen atom (H) or an acetyl group ($CH_3CO$), and $R^6$ is an alkyl group.

The cellulose derivative contained in the first composition may be any as long as it has a liquid crystalline functional group, but may have an ionic moiety as a chemical structure in common with the ionic liquid.

The ionic liquid is a salt present in a liquid state and generally has an ionic size (the size of an atomic group functioning as an ion) larger than that of a normal salt in the form of a solid. By including the ionic moiety as a chemical structure in common with such an ionic liquid, the cellulose derivative has excellent affinity for a polar solvent such as water.

Due to this, for example, in the case where the first composition contains a cellulose derivative in the form of a solid (for example, particles), and further contains a polar solvent such as water as the liquid component, the dispersibility of the cellulose derivative in the first composition can be made excellent. As a result, the fluidity and the ease of handling (handleability) of the first composition can be made more excellent, and the productivity of the shaped article can be made more excellent. Further, in the shaped article production method as described in detail later, the occurrence of an undesirable variation in the thickness of the layer can be more effectively prevented, and therefore, the dimensional accuracy of the shaped article can be made more excellent. Further, the hydrophilicity of the shaped article can be made more excellent, and for example, the shaped article can be favorably applied to a medical device or the like.

Further, in the case where the first composition contains a component with higher polarity such as anionic liquid as the liquid component, in the first composition, the cellulose derivative can be converted to a dissolved state. Due to this, for example, the fluidity of the first composition can be made more excellent, and therefore, the first composition can be favorably ejected or the like by, for example, an inkjet method. As a result, the first composition can be more favorably applied to the production of a shaped article having a finer structure or the like.

Examples of a cation constituting the ionic liquid include various cations such as imidazole-based, pyridine-based, alicyclic amine-based, and aliphatic amine-based cations.

Examples of an anion constituting the ionic liquid include various anions such as halogen-based anions (such as bromide anions and triflate anions), boron-based anions (such as tetraphenyl borate anions), and phosphorus-based anions (such as hexafluorophosphate anions).

Specific examples of the ionic liquid include N-methyl-N-propylpyrrolidinium bis(fluorosulfonyl)imide, 1-ethyl-3-methylimidazolium bis(trifluoromethylsulfonyl)imide, 1-ethyl-3-methylimidazolium bis(fluorosulfonyl)imide, dimethylpropylimidazolium iodide, butylmethylimidazolium iodide, 1,2-dimethyl-3-n-propylimidazolium iodide, 1-methyl-3-n-hexylimidazolium iodide, 1,2-dimethyl-3-ethylimidazolium trifluoromethanesulfonate, 1-methyl-3-butylimidazolium nonafluorobutylsulfonate, 1-methyl-3-ethylimidazolium bis(trifluoromethyl)sulfonylimide, 1-methyl-3-n-hexylimidazolium bis(trifluoromethyl)sulfonylimide, 1-methyl-3-n-hexylimidazolium dicyanamide, lithium bis-fluorosulfonylimide (LiFSI), lithium bis(trifluoromethane-sulfonyl)imide (LiTFSI), 1-methyl-3-propylimidazolium bis(trifluorosulfonyl)imide, 1-ethyl-3-butylimidazolium tetrafluoroborate, and 1-hexyl-3-methylimidazolium hexafluorophosphate.

In particular, the ionic moiety of the cellulose derivative preferably has an imidazolium salt structure.

According to this, the effect of having the ionic moiety as described above is more remarkably exhibited.

Examples of the ionic moiety include a moiety represented by the following formula (3).

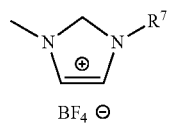

(3)

In the formula (3), $R^7$ is a hydrogen atom (H) or an alkyl group.

The ionic moiety may be introduced into any position of the cellulose derivative, but is preferably introduced into a hydroxy group bonded to the carbon atom at position 6 of β-glucose constituting cellulose by a chemical reaction. That is, it is preferred that the ionic moiety is introduced into $R^3$ in the following formula (2).

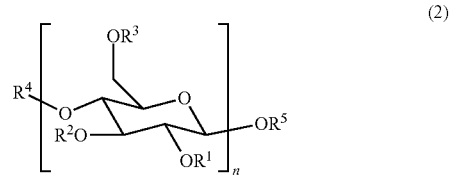

(2)

In the formula (2), $R^1$, $R^2$, $R^3$, $R^4$, and $R^5$ each independently represent a hydrogen atom or a substituent, provided that at least one functional group including the ionic moiety is introduced into the molecule.

According to this, the ionic moiety can be efficiently exposed to the outside of the molecule of the cellulose derivative, and the effect as described above can be more remarkably exhibited. Further, the synthesis of the cellulose derivative as the constituent component of the first composition can be efficiently performed. As a result, this configuration can also contribute to the reduction of the production cost of the shaped article.

It is preferred that a plurality of ionic moieties are introduced into the molecule of the cellulose derivative.

According to this, the effect of having the ionic moiety as described above is more remarkably exhibited.

In particular, it is preferred that a plurality of ionic moieties are introduced into a repeating unit of a polymer chain (side chain) having a repeating structure introduced into a cellulose backbone structure (basic structure).

According to this, the effect of having the ionic moiety as described above is more remarkably exhibited. Further, the synthesis of the cellulose derivative as the constituent component of the first composition can be efficiently performed. As a result, this configuration can also contribute to the reduction of the production cost of the shaped article.

Specific examples of a preferred cellulose derivative satisfying such conditions include a cellulose derivative represented by the following formula (17).

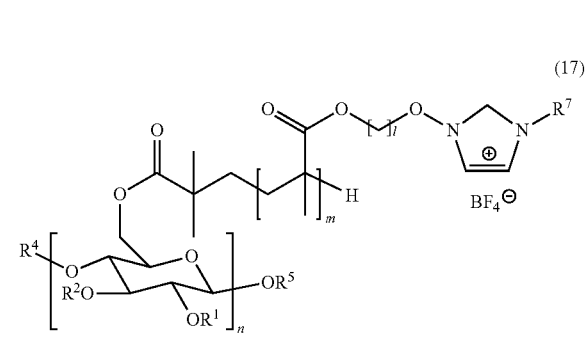

(17)

In the formula (17), n and m are each independently an integer of 2 or more, l is an integer of 1 or more, $R^1$, $R^2$, $R^4$, and $R^5$ are each independently a hydrogen atom (H) or an acetyl group (CH$_3$CO), and $R^7$ is a hydrogen atom (H) or an alkyl group.

It is preferred that the cellulose derivative has the liquid crystalline functional groups and the ionic moieties in the form of blocks, respectively. In other words, it is preferred that the cellulose derivative has a block containing a plurality of liquid crystalline functional groups and a block containing a plurality of ionic moieties.

According to this, both of the effect of having a plurality of liquid crystalline functional groups and the effect of having a plurality of ionic moieties can be more remarkably exhibited, and thus, the dimensional accuracy, mechanical strength, and the like of the shaped article to be produced can be made more excellent.

Specific examples of a preferred cellulose derivative satisfying such conditions include a cellulose derivative represented by the following formula (18).

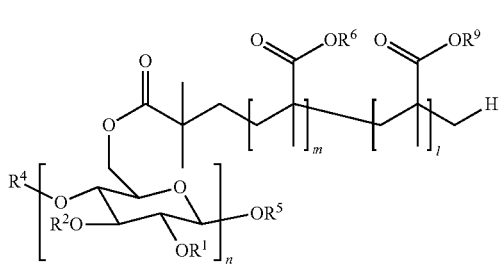

In the formula (18), l, m, and n are each independently an integer of 2 or more, $R^1$, $R^2$, $R^4$, and $R^5$ are each independently a hydrogen atom (H) or an acetyl group ($CH_3CO$), $R^8$ is a group represented by the following formula (9), and $R^9$ is a group represented by the following formula (10) or (11).

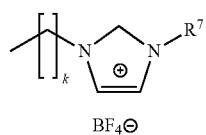

In the formula (9), k is an integer of 1 or more, and $R^7$ is a hydrogen atom (H) or an alkyl group.

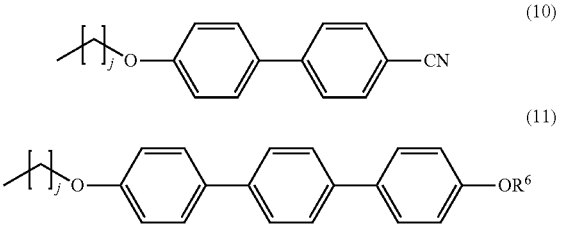

In the formulae (10) and (11), j is an integer of 1 or more, and $R^6$ is a hydrogen atom (H) or an alkyl group.

Further, the cellulose derivative may have a functional group (reactive functional group) which binds the molecular chains of the cellulose derivative through a covalent bond.

In this manner, by binding the molecules of the cellulose derivative through a covalent bond, the advantageous characteristics (for example, high strength, light weight, biosafety, environmental safety, etc.) intrinsic to the cellulosic material can be more effectively exhibited while effectively preventing a decrease in the strength or the like due to separation or the like between the molecules. Further, the mechanical strength, durability, and reliability of the shaped article to be obtained finally can be made more excellent.

Further, for example, by interlacing a molecular chain formed by a chemical reaction involving the reactive functional group of the liquid crystalline compound (a constituent component of the second composition, which will be described in detail later) with a molecular chain formed by a reaction between the cellulose derivatives, the mechanical strength, durability, and the like of the shaped article to be obtained finally can be made further more excellent.

Such a functional group (reactive functional group) of the cellulose derivative may be a group which directly binds the molecules of the cellulose derivative or may be a group which binds the molecules of the cellulose derivative through another atom (at least one atom). More specifically, for example, the functional group of the cellulose derivative may be a group which reacts with the reactive functional group of the liquid crystalline compound, which is a constituent component of the second composition.

Examples of the functional group (reactive functional group) include a group containing a carbon-carbon double bond, a hydroxy group, and a carboxyl group, however, a group containing a carbon-carbon double bond is preferred.

According to this, the reactivity of the cellulose derivative can be made excellent, and the productivity of the shaped article to be produced using the composition set according to the invention can be made more excellent. In addition, the unreacted cellulose derivative can be effectively prevented from being undesirably contained much in the shaped article to be produced. Further, the chemical stability of the covalent bond to be formed by the reaction can be made more excellent. As a result, the strength, durability, and reliability of the shaped article can be made more excellent. Further, the range of choice of a compound which reacts with the cellulose derivative (a compound which can react with the reactive functional group of the cellulose derivative) is expanded, and thus, the range of design of the shaped article is expanded.

Examples of the functional group (reactive functional group) containing a carbon-carbon double bond include a vinyl group and a (meth)acryloyl group, however, a (meth)acryloyl group is preferred.

According to this, the reactivity of the cellulose derivative can be made further more excellent, and thus, the productivity of the shaped article can be made further more excellent. In addition, the unreacted cellulose derivative can be more effectively prevented from being undesirably contained much in the final shaped article. Further, the chemical stability of the covalent bond to be formed by the reaction can be made more excellent. As a result, the strength, durability, and reliability of the shaped article can be made further more excellent. Further, the range of choice of a compound which reacts with the cellulose derivative (a compound which can react with the reactive functional group of the cellulose derivative) is expanded, and thus, the range of design of the shaped article is expanded.

The reactive functional group may be introduced into any position of the cellulose derivative, but is preferably introduced into a side chain of the cellulose derivative different from the cellulose backbone structure (basic backbone structure).

According to this, the effect of having the reactive functional group can be exhibited while more effectively exhibiting the advantageous characteristics (for example, high strength, light weight, biosafety, environmental safety, etc.) intrinsic to cellulose. Further, the side chain of the cellulose derivative generally has higher reactivity than the cellulose backbone structure (basic backbone structure), and therefore, the reaction involving the reactive functional group can be allowed to proceed more efficiently.

In particular, the reactive functional group is preferably introduced into a hydroxy group bonded to the carbon atom at position 6 of β-glucose constituting cellulose by a chemical reaction. That is, it is preferred that the reactive functional group is introduced into $R^3$ in the above formula (2).

According to this, the steric hindrance of the reactive functional group can be made small, or the like, and thus, the reactivity of the cellulose derivative can be made excellent, and thus, the productivity of the shaped article can be made more excellent. In addition, the unreacted cellulose derivative can be prevented from being undesirably contained much in the final shaped article. Accordingly, the strength, durability, and reliability of the shaped article can be made more excellent. Further, the synthesis of the cellulose derivative as the constituent component of the first composition can be efficiently performed. As a result, this configuration can also contribute to the reduction of the production cost of the shaped article.

Further, the reactive functional group is preferably introduced into the cellulose backbone through at least one carbon-carbon single bond in the basic cellulose structure.

According to this, the reactivity of the reactive functional group can be made more excellent, and thus, the productivity and the like of the shaped article can be made more excellent.

Specific examples of a preferred cellulose derivative satisfying the conditions as described above include cellulose derivatives represented by the following formulae (12), (13), and (14).

each independently a hydrogen atom (H) or an acetyl group ($CH_3CO$), and $R^8$ is a group represented by the above formula (9).

When the cellulose derivative is a cellulose derivative represented by any of the formulae (12) to (14), the effect as described above is more remarkably exhibited.

It is preferred that the reaction to bond the molecular chains of the cellulose derivative through a covalent bond proceeds by UV irradiation.

According to this, the productivity of the shaped article can be made more excellent while more effectively preventing undesirable denaturation, deterioration, or the like of the materials. Further, the structure of the production apparatus for the shaped article can be prevented from being complicated, and thus, the production cost of the shaped article can be kept low.

It is preferred that the cellulose derivative (particularly, the cellulose derivative in which the reactive functional group contains a carbon-carbon double bond) reacts with a siloxane compound having two or more Si—H bonds in the molecule.

According to this, the efficiency of the formation of the covalent bond can be made more excellent, and thus, the productivity of the shaped article can be made more excellent. In addition, the unreacted cellulose derivative can be effectively prevented from being undesirably contained

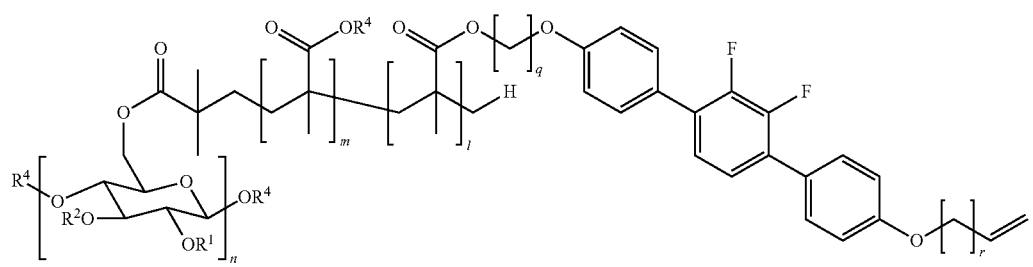

(12)

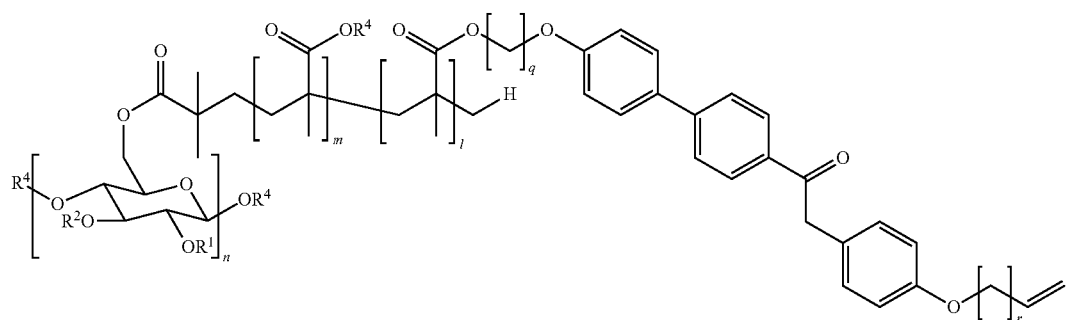

(13)

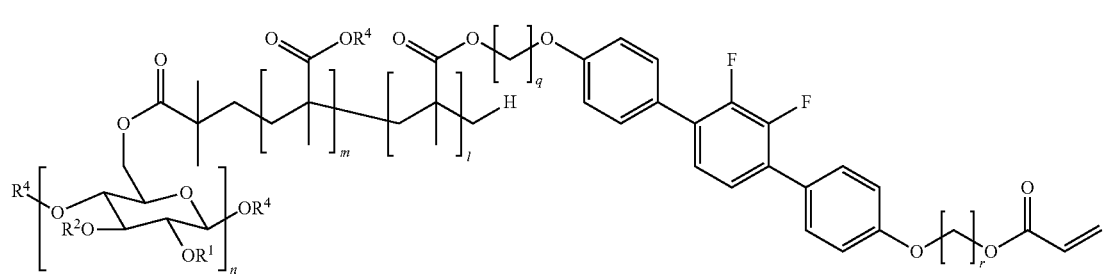

(14)

In the formulae (12), (13), and (14), l, m, and n are each independently an integer of 2 or more, q and r are each independently an integer of 1 or more, $R^1$, $R^2$, $R^4$, and $R^5$ are much in the shaped article. Further, the chemical stability of the covalent bond to be formed by the reaction can be made more excellent. As a result, the strength, durability, and reliability of the shaped article can be made more excellent. Further, the chemical reaction to form the covalent bond by heating can be favorably performed.

The siloxane compound with which the cellulose derivative reacts preferably has two or more Si—H bonds in the molecule, but more preferably has three or more Si—H bonds in the molecule.

According to this, a more complicated net structure can be formed by the chemical reaction to form the covalent bond, and thus, the strength, durability, and the like of the shaped article can be made more excellent.

The siloxane compound with which the cellulose derivative reacts may be a chain compound, but is preferably a cyclic compound.

According to this, the strength, durability, and the like of the shaped article can be made more excellent.

Examples of the siloxane compound (the siloxane compound which reacts with the cellulose derivative) satisfying such conditions include a siloxane compound represented by the following formula (4).

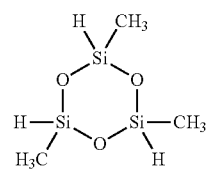

(4)

The cellulose derivative (particularly, the cellulose derivative in which the reactive functional group contains a carbon-carbon double bond) may be a cellulose derivative which reacts with a crosslinking agent.

According to this, for example, a more complicated net structure can be formed by the chemical reaction to form the covalent bond, and thus, the strength, durability, and the like of the shaped article can be made more excellent. Further, for example, by irradiation with a light such as a UV light, the chemical reaction to form the covalent bond can be favorably performed.

Examples of the crosslinking agent include compounds having a polymerizable functional group such as a vinyl group or a (meth)acryloyl group.

Among these, as the crosslinking agent, a compound having a plurality of polymerizable functional groups in the molecule is preferred, and a compound in which an alkyl chain is modified with a polymerizable functional group at both ends is more preferred.

Examples of such a crosslinking agent include a compound represented by the following formula (5).

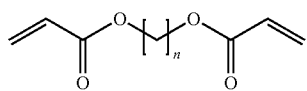

(5)

In the formula (5), n is an integer of 1 or more.

The weight average molecular weight of the cellulose derivative contained in the first composition is not particularly limited, but is preferably 5,000 or more and 10,000,000 or less, more preferably 10,000 or more and 7,000,000 or less.

According to this, the strength, durability, and reliability of the shaped article to be produced can be made more excellent.

The form of the cellulose derivative in the first composition is not particularly limited, and the cellulose derivative may be contained in a solid state, or may be contained in a liquid state (in a dissolved state or the like), or may be in a mixed state of these states. However, it is preferred to contain particles whose surfaces are at least partially constituted by the cellulose derivative.

According to this, for example, by using the production method as described later, a shaped article having stable quality and properties can be produced more stably and more efficiently.

In the case where the first composition contains particles whose surfaces are at least partially constituted by the cellulose derivative, the average particle diameter of the particles is not particularly limited, but is preferably 1 μm or more and 25 μm or less, more preferably 1 μm or more and 15 μm or less.

According to this, the mechanical strength of the shaped article can be made more excellent, and also the dimensional accuracy of the shaped article can be made more excellent. Further, the fluidity of the first composition can be made more excellent, and thus, the productivity of the shaped article can be made more excellent.

The "average particle diameter" as used herein refers to an average particle diameter on a volume basis and can be determined by, for example, adding a sample to methanol, followed by dispersion for 3 minutes using an ultrasonic disperser, and then, measuring the resulting dispersion liquid using a particle size distribution analyzer employing a Coulter counter method (for example, model TA-II, manufactured by Coulter Electronics, Inc., or the like) with an aperture of 50 μm.

The particles may have any shape, but preferably have a spherical shape. According to this, the fluidity of the first composition can be made more excellent, and thus, the productivity of the shaped article can be made more excellent, and also the occurrence of undesirable irregularities or the like in the shaped article to be produced is more effectively prevented, and the dimensional accuracy of the shaped article can be made more excellent.

The content of the particles in the first composition is not particularly limited, but is preferably 8% by mass or more and 90% by mass or less, more preferably 10% by mass or more and 80% by mass or less.

According to this, while making the fluidity of the first composition excellent, the strength, durability, reliability, and the like of the shaped article can be made more excellent.

The content of the cellulose derivative with respect to the total solid content in the first composition is not particularly limited, but is preferably 20% by mass or more, more preferably 40% by mass or more and 99% by mass or less.

According to this, while making the productivity, dimensional accuracy, and the like of the shaped article excellent, the strength, durability, reliability, and the like of the shaped article can be made more excellent.

Liquid Component

The first composition may contain a liquid component having a function to dissolve or disperse the cellulose derivative as a component other than the above-mentioned cellulose derivative.

According to this, for example, the fluidity of the first composition can be increased, and the first composition can be formed into a liquid or a paste. As a result, the productivity of the shaped article can be made more excellent. Further, in the case where the first composition contains particles (for example, particles constituted by a material containing the cellulose derivative), undesirable scattering or the like of the particles when forming the shaped article can be effectively prevented.

In particular, in the case where the first composition contains an aqueous solvent as the liquid component, the following effects are obtained.

That is, since the aqueous solvent has high affinity for water, in the case where the first composition contains a water-soluble resin (which will be described later), the water-soluble resin can be favorably dissolved. According to this, the fluidity of the first composition can be made favorable, and thus, the productivity, dimensional accuracy, and the like of the shaped article can be made more excellent.

Further, in the case where the shaped article is produced using the method as described in detail later, an undesirable variation in the thickness of the layer to be formed using the first composition can be more effectively prevented. Further, when the layer in a state where the aqueous solvent is removed is formed, the water-soluble resin can be adhered to the particles with higher uniformity throughout the entire layer, and thus, the occurrence of an undesirable unevenness in the composition can be more effectively prevented. Due to this, the occurrence of an undesirable variation in the mechanical strength among the individual regions of the shaped article to be obtained finally can be more effectively prevented, and thus, the reliability of the shaped article can be further increased.

The "aqueous solvent" as used herein refers to water or a liquid having high affinity for water, and specifically refers to a solvent having a solubility in 100 g of water at 25° C. of 50 g or more.

Examples of the aqueous solvent include water; alcoholic solvents such as methanol, ethanol, and isopropanol; ketone-based solvents such as methyl ethyl ketone and acetone; glycol ether-based solvents such as ethylene glycol monoethyl ether and ethylene glycol monobutyl ether; glycol ether acetate-based solvents such as propylene glycol 1-monomethyl ether 2-acetate and propylene glycol 1-monoethyl ether 2-acetate; polyethylene glycol, polypropylene glycol; and ionic liquids, and one solvent or a combination of two or more solvents selected from these can be used.

Above all, the first composition preferably contains water.

According to this, the water-soluble resin can be more reliably dissolved, and the fluidity of the first composition and the uniformity of the composition of the layer to be formed using the first composition can be made more excellent. Further, water is a component which is easily removed. In addition, water is advantageous also from the viewpoint of safety for the human body, environmental problems, and the like.

The content of the liquid component (a component functioning as a solvent or a dispersion medium) in the first composition is preferably 9% by mass or more and 92% by mass or less, more preferably 15% by mass or more and 89% by mass or less.

According to this, the effect of including the liquid component as described above is more remarkably exhibited, and also the liquid component can be easily removed in a shorter time in the production process for the shaped article, and thus, the productivity of the shaped article can be made more excellent. Further, in the case where the shaped article is produced using the method as described in detail later, in the layer in a state where the liquid component is removed, voids can be incorporated at an appropriate ratio, and thus, the permeability of the second composition can be made more excellent, and as a result, the mechanical strength, dimensional accuracy, and the like of the shaped article to be obtained finally can be made more excellent.

In the case where the aqueous solvent contains water, the content of water in the aqueous solvent is preferably 80% by mass or more, more preferably 90% by mass or more.

According to this, the effect as described above is more remarkably exhibited.

Binder

The first composition may contain a binder.

According to this, for example, in the case where the shaped article is produced using the method as described in detail later, a plurality of particles (particles whose surfaces are at least partially constituted by the cellulose derivative) can be favorably bound (temporarily fixed) to one another, and thus, undesirable scattering or the like of the particles can be effectively prevented. As a result, the safety for workers and the dimensional accuracy of the shaped article to be produced can be further improved.

In the case where the first composition contains a binder, the binder is preferably dissolved in the liquid component as described above in the first composition.

According to this, the fluidity of the first composition can be made more favorable.

Further, in the case where the shaped article is produced using the method as described in detail later, an undesirable variation in the thickness of the layer to be formed using the first composition can be more effectively prevented. Further, in a state where the liquid component is removed from the layer, the binder can be adhered to the particles with higher uniformity throughout the entire layer, and thus, the occurrence of an undesirable unevenness in the composition can be more effectively prevented. Due to this, the occurrence of an undesirable variation in the mechanical strength among the individual regions of the shaped article to be obtained finally can be more effectively prevented, and thus, the reliability of the shaped article can be further increased.

As the binder, a binder having a function to temporarily fix a plurality of particles in the layer formed using the first composition (particularly the layer in a state where the liquid component is removed) can be used, and in particular, a water-soluble resin can be favorably used.

By including a water-soluble resin, in the case where the first composition contains an aqueous solvent (particularly water), the binder (water-soluble resin) can be included in the first composition in a dissolved state, and thus, the fluidity and handleability (ease of handling) of the first composition can be made more excellent. As a result, the productivity of the shaped article can be made more excellent.

Further, in the case where the shaped article is produced using the method as described in detail later, a region of the layer to which the second composition is not applied in the production process for the shaped article can be easily and efficiently removed by applying an aqueous solvent (particularly water) thereto. As a result, the productivity of the shaped article can be made more excellent. Further, the region of the layer which should be removed can be easily and reliably prevented from adhering to or remaining in the finally obtained shaped article, and thus, the dimensional accuracy of the shaped article can be made more excellent.

Hereinafter, the water-soluble resin as the binder will be mainly described.

The water-soluble resin may be any as long as it can be at least partially dissolved in an aqueous solvent, but is preferably, for example, a resin having a solubility in water (the mass of a resin that can be dissolved in 100 g of water) at 25° C. of 5 g/100 g of water or more, more preferably a resin having a solubility in water at 25° C. of 10 g/100 g of water or more.

Examples of the water-soluble resin include synthetic polymers such as polyvinyl alcohol (PVA), polyvinylpyrrolidone (PVP), polycaprolactone diol, sodium polyacrylate, ammonium polyacrylate, polyacrylamide, modified polyamide, polyethylenimine, polyethylene oxide, and a random copolymer of ethylene oxide and propylene oxide; natural polymers such as corn starch, mannan, pectin, agar, alginic acid, dextran, glue, and gelatin; and semisynthetic polymers such as carboxymethyl cellulose, hydroxyethyl cellulose, oxidized starch, and modified starch, and one material or a combination of two or more materials selected from these can be used.

Above all, in the case where the water-soluble resin as the binder is polyvinyl alcohol, the mechanical strength of the shaped article can be made more excellent. Further, by adjusting the saponification degree or the polymerization degree, the properties (for example, water solubility, water resistance, etc.) of the binder and the properties (for example, viscosity, the ability to fix the particles, wettability, etc.) of the first composition can be more favorably controlled. Due to this, polyvinyl alcohol can be more favorably applied to the production of a variety of shaped articles. Further, polyvinyl alcohol is inexpensive and offers a stable supply among the various water-soluble resins. Due to this, while keeping the production cost low, the shaped article can be stably produced.

In the case where the water-soluble resin as the binder contains polyvinyl alcohol, the saponification degree of the polyvinyl alcohol is preferably 85 or more and 90 or less. According to this, a decrease in the solubility of polyvinyl alcohol in an aqueous solvent (particularly water) can be prevented. Due to this, in the case where the first composition contains an aqueous solvent (particularly water), a decrease in the adhesiveness between adjacent layers can be more effectively prevented.

In the case where the water-soluble resin as the binder contains polyvinyl alcohol, the polymerization degree of the polyvinyl alcohol is preferably 300 or more and 1,000 or less. According to this, in the case where the first composition contains an aqueous solvent (particularly water), the mechanical strength of the respective layers and the adhesiveness between adjacent layers can be made more excellent.

Further, in the case where the water-soluble resin as the binder is polyvinylpyrrolidone (PVP), effects as described below are obtained. That is, polyvinylpyrrolidone has excellent adhesiveness to various materials such as a glass, a metal, and a plastic, and therefore, the strength and the stability of the shape of a portion of the layer to which the second composition is not applied can be made more excellent, and the dimensional accuracy of the shaped article to be obtained finally can be made more excellent. Further, polyvinylpyrrolidone shows high solubility in various organic solvents, and therefore, in the case where the first composition contains an organic solvent, the fluidity of the first composition can be made more excellent, and a layer in which an undesirable variation in the thickness is more effectively prevented can be favorably formed, and thus, the dimensional accuracy of the shaped article to be obtained finally can be made more excellent. Further, polyvinylpyrrolidone shows high solubility in an aqueous solvent (particularly water), and therefore, in an unbound particle removal step (after completion of shaping), among the particles constituting the respective layers, the particles which are not bound to one another by a solidified material (cured material) of the second composition can be easily and reliably removed. Further, polyvinylpyrrolidone has excellent affinity for various coloring agents, and therefore, in the case where the second composition containing a coloring agent is used in the second composition application step, undesirable diffusion of the coloring agent can be effectively prevented.

In the case where the water-soluble resin as the binder contains polyvinylpyrrolidone, the weight average molecular weight of the polyvinylpyrrolidone is preferably 10,000 or more 1,700,000 or less, more preferably 30,000 or more 1,500,000 or less.

According to this, the above-mentioned function can be more effectively exhibited.

In the case where the water-soluble resin as the binder contains polycaprolactone diol, the weight average molecular weight of the polycaprolactone diol is preferably 10,000 or more 1,700,000 or less, more preferably 30,000 or more 1,500,000 or less.

According to this, the above-mentioned function can be more effectively exhibited.

In the first composition, the binder is preferably in a liquid state (for example, in a dissolved state, in a molten state, or the like) in the layer forming step of the method as will be described in detail later. According to this, the uniformity of the thickness of the layer to be formed using the first composition can be easily and reliably further increased.

In the case where the first composition contains a binder, the content of the binder in the first composition is preferably 0.5% by mass or more and 25% by mass or less, more preferably 1.0% by mass or more and 10% by mass or less.

According to this, the effect of including the binder as described above is more remarkably exhibited, and also the content of the cellulose derivative and the like in the first composition can be made sufficiently high, and thus, the productivity of the shaped article, the mechanical strength and the like of the shaped article to be produced can be made more excellent.

Other Component

Further, the first composition may contain a component (another component) other than the above-mentioned components. Examples of such a component include a polymerization initiator, a polymerization accelerator, a crosslinking agent, a siloxane compound, a permeation accelerator, a wetting agent (humectant), a fixing agent, an antifungal agent, a preservative, an antioxidant, a UV absorber, a chelating agent, a pH adjusting agent, particles constituted by a material other than the above-mentioned cellulose derivative, and a liquid crystalline compound which will be described in detail later.

Examples of a constituent material of the particles constituted by a material other than the above-mentioned cellulose derivative include an inorganic material, an organic material (excluding the above-mentioned cellulose derivative having a liquid crystalline functional group), and a composite of these materials.

Examples of the inorganic material constituting the particles include various metals and metal compounds. Examples of the metal compounds include various metal oxides such as silica, alumina, titanium oxide, zinc oxide, zirconium oxide, tin oxide, magnesium oxide, and potassium titanate; various metal hydroxides such as magnesium hydroxide, aluminum hydroxide, and calcium hydroxide; various metal nitrides such as silicon nitride, titanium nitride, and aluminum nitride; various metal carbides such as silicon carbide and titanium carbide; various metal sulfides such as zinc sulfide; various metal carbonates such as calcium carbonate and magnesium carbonate; various metal sulfates such as calcium sulfate and magnesium sulfate; various metal silicates such as calcium silicate and magnesium silicate; various metal phosphates such as calcium phosphate; various metal borates such as aluminum borate and magnesium borate; composites of these materials; and gypsum (various hydrates of calcium sulfate and anhydrides of calcium sulfate).

Examples of the organic material constituting the particles include synthetic resins and natural polymers, and more specific examples thereof include a polyethylene resin; polypropylene; polyethylene oxide; polypropylene oxide; polyethylenimine; polystyrene; polyurethane; polyurea; polyester; a silicone resin; an acrylic silicone resin; a polymer containing a (meth)acrylate ester as a constituent monomer such as methyl polymethacrylate; a crosspolymer (an ethylene acrylic acid copolymer resin or the like) containing a (meth)acrylate ester as a constituent monomer such as a methyl methacrylate crosspolymer; polyamide resins such as nylon 12, nylon 6, and copolymer nylon; polyimide; cellulose; cellulose derivatives (cellulose derivatives other than the above-mentioned cellulose derivative having a liquid crystalline functional group) such as carboxymethyl cellulose; gelatin; starch; chitin; and chitosan.

In the production of the shaped article, a plurality of types of first compositions may be used.

For example, by using a plurality of types of first compositions having different types or contents of the cellulose derivative, the properties such as rigidity and elasticity required for the respective regions of the shaped article can be favorably adjusted.

Second Composition
Liquid Crystalline Compound

As described above, the second composition contains a liquid crystalline compound having a reactive functional group and can be in a liquid state.

According to this, the first composition and the second composition can be favorably brought into contact with each other, and in the case where the first composition and the second composition come in contact with each other, the liquid crystalline functional group of the cellulose derivative and the liquid crystalline moiety (liquid crystalline functional group) of the liquid crystalline compound can be favorably aligned. Then, by reacting the reactive functional group of the liquid crystalline compound, the liquid crystalline compound is solidified (cured) while maintaining the alignment state as described above. Due to this, the mechanical strength, durability, reliability, and the like of the shaped article to be obtained can be made excellent.

The phrase "can be in a liquid state" as used herein is a concept including, for example, a material which is in a liquid state even if it is not particularly subjected to a treatment, a material which is in a solid state at room temperature or the like, but can be converted to a liquid state by a treatment such as heating.

The liquid crystalline compound contained in the second composition includes a liquid crystalline moiety (liquid crystalline functional group) as described above.

Examples of the liquid crystalline functional group (atomic group) included in the liquid crystalline compound include groups represented by the above formulae (6).

The liquid crystalline functional group of the cellulose derivative and the liquid crystalline functional group of the liquid crystalline compound may be the same or different, but are preferably the same. According to this, the affinity between the cellulose derivative and the liquid crystalline compound can be made more excellent, and the effect as described above is more remarkably exhibited.

The liquid crystalline compound has a reactive functional group in addition to a liquid crystalline functional group.

The reactive functional group of the liquid crystalline compound is a functional group contributing to the chemical reaction to form the covalent bond.

Examples of the reactive functional group of the liquid crystalline compound include a group containing a carbon-carbon double bond, a hydroxy group, and a carboxyl group, however, a group containing a carbon-carbon double bond is preferred.

According to this, the reactivity of the liquid crystalline compound can be made excellent, and the productivity of the shaped article can be made more excellent. In addition, the unreacted liquid crystalline compound can be effectively prevented from being undesirably contained in the shaped article to be produced. Further, the chemical stability of the covalent bond to be formed by the reaction can be made more excellent. As a result, the strength, durability, and reliability of the shaped article can be made more excellent. Further, the range of choice of a compound which reacts with the liquid crystalline compound (a compound which can react with the reactive functional group of the liquid crystalline compound) is expanded, and thus, the range of design of the liquid crystalline compound is expanded.

Examples of the functional group (reactive functional group) containing a carbon-carbon double bond include a vinyl group and a (meth)acryloyl group, however, a (meth)acryloyl group is preferred.

According to this, the reactivity of the liquid crystalline compound can be made further more excellent, and thus, the productivity of the shaped article can be made further more excellent. In addition, the unreacted liquid crystalline compound can be more effectively prevented from being undesirably contained in the final shaped article. Further, the chemical stability of the covalent bond to be formed by the reaction can be made more excellent. As a result, the strength, durability, and reliability of the shaped article can be made further more excellent. Further, the range of choice of a compound which reacts with the liquid crystalline compound (a compound which can react with the reactive functional group of the liquid crystalline compound) is expanded, and thus, the range of design of the liquid crystalline compound is further expanded.

Specific examples of a preferred liquid crystalline compound satisfying the conditions as described above include compounds represented by the following formulae (15) and (16).

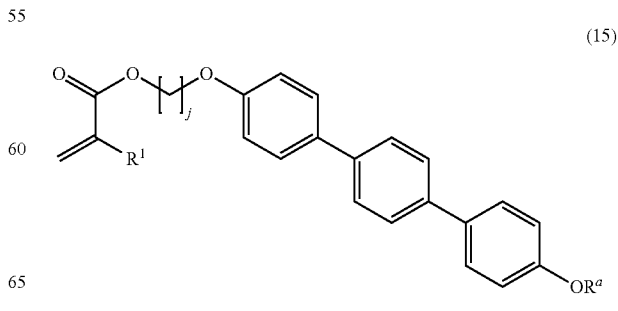

(15)

In the formula (15), j is an integer of 1 or more, $R^1$ is a hydrogen atom (H) or a methyl group, and $R^6$ is a hydrogen atom (H) or an alkyl group.

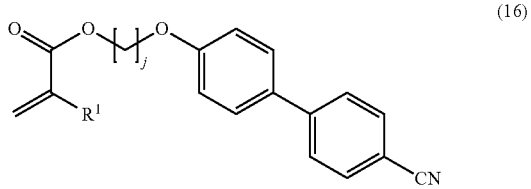

(16)

In the formula (16), j is an integer of 1 or more, and $R^1$ is a hydrogen atom (H) or a methyl group.

When the liquid crystalline compound is a compound represented by the formula (15) or (16), the effect as described above is more remarkably exhibited.

The liquid crystalline compound may be a compound which reacts with a siloxane compound having two or more Si—H bonds in the molecule as described above or the like.

According to this, the same effect as described above is obtained.

It is preferred that the chemical reaction involving the reactive functional group of the liquid crystalline compound proceeds by UV irradiation.

According to this, the productivity of the shaped article can be made more excellent while more effectively preventing undesirable denaturation, deterioration, or the like of the materials. Further, the structure of the production apparatus for the shaped article can be prevented from being complicated, and thus, the production cost of the shaped article can be kept low.

The liquid crystalline compound may at least partially react with the cellulose derivative to form a covalent bond with the cellulose derivative.

The content of the liquid crystalline compound in the second composition is not particularly limited, but is preferably 50% by mass or more, more preferably 70% by mass or more, further more preferably 85% by mass or more.

According to this, the effect of using the liquid crystalline compound as described above is more remarkably exhibited.

Other Component

The second composition may contain a component (another component) other than the above-mentioned components. Examples of such a component include various coloring agents such as a pigment and a dye, various fluorescent materials, various light storage materials, various phosphorescent materials, an infrared absorbing material, a dispersant, a surfactant, a curable resin other than the liquid crystalline compound, a polymerization initiator, a polymerization accelerator, a crosslinking agent, a siloxane compound, a liquid component other than the above-mentioned liquid crystalline compound (particularly, a polar solvent such as water or an ionic liquid), a cellulose derivative (including the above-mentioned cellulose derivative having a liquid crystalline functional group) or cellulose which is not chemically modified, a permeation accelerator, a wetting agent (humectant), a fixing agent, an antifungal agent, a preservative, an antioxidant, a UV absorber, a chelating agent, a pH adjusting agent, a thickening agent, a filler, an anti-aggregation agent, and a defoaming agent.

By including a coloring agent in the second composition, the shaped article colored in a color corresponding to the color of the coloring agent can be obtained.

In particular, by including a pigment as the coloring agent, the light resistance of the second composition and the shaped article can be made favorable. As the pigment, either of an inorganic pigment and an organic pigment can be used.

Examples of the inorganic pigment include carbon blacks (C.I. Pigment Black 7) such as Furnace Black, Lamp Black, Acetylene Black, and Channel Black, iron oxide, and titanium oxide, and one pigment or a combination of two or more pigments selected from these can be used.

Among the inorganic pigments described above, in order to take on a preferred white color, titanium oxide is preferred.

Examples of the organic pigment include azo pigments such as insoluble azo pigments, condensed azo pigments, azo lakes, and chelate azo pigments, polycyclic pigments such as phthalocyanine pigments, perylene and perinone pigments, anthraquinone pigments, quinacridone pigments, dioxane pigments, thioindigo pigments, isoindolinone pigments, and quinophthalone pigments, dye chelates (for example, basic dye type chelates, acidic dye type chelates, etc.), dye lakes (basic dye type lakes and acidic dye type lakes), nitro pigments, nitroso pigments, aniline black, and daylight fluorescent pigments, and one pigment or a combination of two or more pigments selected from these can be used.

Examples of a white pigment include C.I. Pigment White 6, 18, and 21.

Examples of a yellow pigment include C.I. Pigment Yellow 1, 2, 3, 4, 5, 6, 7, 10, 11, 12, 13, 14, 16, 17, 24, 34, 35, 37, 53, 55, 65, 73, 74, 75, 81, 83, 93, 94, 95, 97, 98, 99, 108, 109, 110, 113, 114, 117, 120, 124, 128, 129, 133, 138, 139, 147, 151, 153, 154, 167, 172, and 180.

Examples of a magenta pigment include C.I. Pigment Red 1, 2, 3, 4, 5, 6, 7, 8, 9, 10, 11, 12, 14, 15, 16, 17, 18, 19, 21, 22, 23, 30, 31, 32, 37, 38, 40, 41, 42, 48 (Ca), 48 (Mn), 57 (Ca), 57:1, 88, 112, 114, 122, 123, 144, 146, 149, 150, 166, 168, 170, 171, 175, 176, 177, 178, 179, 184, 185, 187, 202, 209, 219, 224, and 245, and C.I. Pigment Violet 19, 23, 32, 33, 36, 38, 43, and 50.

Examples of a cyan pigment include C.I. Pigment Blue 1, 2, 3, 15, 15:1, 15:2, 15:3, 15:34, 15:4, 16, 18, 22, 25, 60, 65, and 66, and C.I. Vat Blue 4 and 60.

Examples of the pigment other than the above-mentioned pigments include C.I. Pigment Green 7 and 10, C.I. Pigment Brown 3, 5, 25, and 26, and C.I. Pigment Orange 1, 2, 5, 7, 13, 14, 15, 16, 24, 34, 36, 38, 40, 43, and 63.

In the case where the second composition contains a pigment, the average particle diameter of the pigment is preferably 300 nm or less, more preferably 50 nm or more and 250 nm or less. According to this, for example, the dispersion stability of the pigment in the second composition and the ejection stability of the second composition can be made more excellent, and also an image with a higher image quality can be formed.

Examples of the dye include acidic dyes, direct dyes, reactive dyes, and basic dyes, and one dye or a combination of two or more dyes selected from these can be used.

Examples of the fluorescent material constituting the second composition include C.I. Direct Yellow 87, C.I. Acid Red 52, C.I. Acid Red 92, Brilliant Sulfo Flavin, Eosin, Basic Flavin, Acridine Orange, Rhodamine 6G, and Rhodamine B.

Examples of the light storage material constituting the second composition include sulfides of alkaline earth metals such as zinc, calcium, strontium, and barium, and light storage materials such as strontium aluminate, or inorganic fluorescent materials such as various sulfides and oxides exemplified by zinc sulfide and the like.

Examples of the phosphorescent material constituting the second composition include an iridium complex and a cyclometallated complex.

Examples of the infrared absorbing material constituting the second composition include ITO and ATO fine particles.

In the case where the second composition contains a dispersoid such as a pigment, if the second composition further contains a dispersant, the dispersibility of the dispersoid can be made more favorable.

The dispersant is not particularly limited, but examples thereof include dispersants which are commonly used for preparing a pigment dispersion liquid such as a polymeric dispersant.

Specific examples of the polymeric dispersant include dispersants containing, as a main component, at least one of polyoxyalkylene polyalkylene polyamine, a vinyl-based polymer or copolymer, an acrylic polymer or copolymer, polyester, polyamide, polyimide, polyurethane, an amino-based polymer, a silicon-containing polymer, a sulfur-containing polymer, a fluorine-containing polymer, and an epoxy resin.

When the second composition contains a surfactant, the abrasion resistance of the shaped article can be made more favorable.

The surfactant is not particularly limited, however, for example, a polyester-modified silicone, a polyether-modified silicone, or the like as a silicone-based surfactant can be used, and in particular, it is preferred to use polyether-modified polydimethylsiloxane or polyester-modified polydimethylsiloxane.

Examples of the curable resin include a thermosetting resin; various photocurable resins such as a visible light curable resin which is cured by a light in the visible light range (a photocurable resin in a narrow sense), a UV curable resin, and an IR curable resin; and an X-ray curable resin, and one curable resin or a combination of two or more curable resins selected from these can be used.

As the UV curable resin (polymerizable compound), a compound whose addition polymerization or ring-opening polymerization is initiated by a radical species, a cationic species, or the like generated from a photopolymerization initiator by UV irradiation, thereby forming a polymer is preferably used. Examples of the polymerization form of the addition polymerization include radical, cationic, anionic, metathesis, and coordination polymerization. Further, examples of the polymerization form of the ring-opening polymerization include cationic, anionic, radical, metathesis, and coordination polymerization.

Examples of an addition polymerizable compound include compounds having at least one ethylenically unsaturated double bond. As the addition polymerizable compound, a compound having at least one, preferably two or more terminal ethylenically unsaturated bonds can be preferably used.

An ethylenically unsaturated polymerizable compound has a chemical form of a monofunctional polymerizable compound, a polyfunctional polymerizable compound, or a mixture thereof.

Examples of the monofunctional polymerizable compound include unsaturated carboxylic acids (for example, acrylic acid, methacrylic acid, itaconic acid, crotonic acid, isocrotonic acid, maleic acid, etc.) and esters thereof, and amides thereof.

As the polyfunctional polymerizable compound, an ester of an unsaturated carboxylic acid with an aliphatic polyhydric alcohol compound or an amide of an unsaturated carboxylic acid with an aliphatic amine compound is used.

Further, an addition reaction product of an ester or an amide of an unsaturated carboxylic acid having a hydroxyl group or a nucleophilic substituent such as an amino group or a mercapto group with an isocyanate or an epoxy, a dehydration condensation reaction product with a carboxylic acid, or the like can also be used. Further, an addition reaction product of an ester or an amide of an unsaturated carboxylic acid having an electrophilic substituent such as an isocyanate group or an epoxy group with an alcohol, an amine, or a thiol, further, a substitution reaction product of an ester or an amide of an unsaturated carboxylic acid having a leaving substituent such as a halogen group or a tosyloxy group with an alcohol, an amine, or a thiol can also be used.

As a specific example of the radical polymerizable compound which is the ester of an unsaturated carboxylic acid with an aliphatic polyhydric alcohol compound, for example, a (meth)acrylate ester is representative, and either a monofunctional (meth)acrylate or a polyfunctional (meth)acrylate can be used.

Specific examples of the monofunctional (meth)acrylate include tolyloxyethyl (meth)acrylate, phenyloxyethyl (meth)acrylate, cyclohexyl (meth)acrylate, ethyl (meth)acrylate, methyl (meth)acrylate, isobornyl (meth)acrylate, tetrahydrofurfuryl (meth)acrylate, ethoxyethoxyethyl (meth)acrylate, 2-(2-vinyloxyethoxy)ethyl (meth)acrylate, 2-hydroxy-3-phenoxypropyl (meth)acrylate, and 4-hydroxybutyl (meth)acrylate.

Specific examples of a difunctional (meth)acrylate include ethylene glycol di(meth)acrylate, triethylene glycol di(meth)acrylate, 1,3-butanediol di(meth)acrylate, tetramethylene glycol di(meth)acrylate, propylene glycol di(meth)acrylate, neopentyl glycol di(meth)acrylate, hexanediol di(meth)acrylate, 1,4-cyclohexanediol di(meth)acrylate, tetraethylene glycol di(meth)acrylate, pentaerythritol di(meth)acrylate, dipentaerythritol di(meth)acrylate, and dipropylene glycol di(meth)acrylate.

Specific examples of a trifunctional (meth)acrylate include trimethylolpropane tri(meth)acrylate, trimethylolethane tri(meth)acrylate, alkylene oxide-modified tri(meth)acrylate of trimethylolpropane, pentaerythritol tri(meth)acrylate, dipentaerythritol tri(meth)acrylate, trimethylolpropane tri((meth)acryloyloxypropyl) ether, isocyanuric acid alkylene oxide-modified tri(meth)acrylate, propionic acid dipentaerythritol tri(meth)acrylate, tri((meth)acryloyloxyethyl) isocyanurate, hydroxypivalaldehyde-modified dimethylolpropane tri(meth)acrylate, and sorbitol tri(meth)acrylate.

Specific examples of a tetrafunctional (meth)acrylate include pentaerythritol tetra(meth)acrylate, sorbitol tetra(meth)acrylate, ditrimethylolpropane tetra(meth)acrylate, propionic acid dipentaerythritol tetra(meth)acrylate, and ethoxylated pentaerythritol tetra(meth)acrylate.

Specific examples of a pentafunctional (meth)acrylate include sorbitol penta(meth)acrylate and dipentaerythritol penta(meth)acrylate.

Specific examples of a hexafunctional (meth)acrylate include dipentaerythritol hexa(meth)acrylate, sorbitol hexa(meth)acrylate, alkylene oxide-modified hexa(meth)acrylate of phosphazene, and caprolactone-modified dipentaerythritol hexa(meth)acrylate.

Examples of the polymerizable compound other than (meth)acrylates include itaconate esters, crotonate esters, isocrotonate esters, and maleate esters.

Examples of the itaconate esters include ethylene glycol diitaconate, propylene glycol diitaconate, 1,3-butanediol diitaconate, 1,4-butanediol diitaconate, tetramethylene glycol diitaconate, pentaerythritol diitaconate, and sorbitol tetraitaconate.

Examples of the crotonate esters include ethylene glycol dicrotonate, tetramethylene glycol dicrotonate, pentaerythritol dicrotonate, and sorbitol tetracrotonate.

Examples of the isocrotonate esters include ethylene glycol diisocrotonate, pentaerythritol diisocrotonate, and sorbitol tetraisocrotonate.

Examples of the maleate esters include ethylene glycol dimaleate, triethylene glycol dimaleate, pentaerythritol dimaleate, and sorbitol tetramaleate.

Specific examples of a monomer of the amide of an unsaturated carboxylic acid with an aliphatic amine compound include methylenebis-acrylamide, methylenebis-methacrylamide, 1,6-hexamethylenebis-acrylamide, 1,6-hexamethylenebis-methacrylamide, diethylenetriamine trisacrylamide, xylylene bisacrylamide, xylylene bismethacrylamide, and (meth)acryloylmorpholine.

A urethane-based addition polymerizable compound which is produced by an addition reaction between an isocyanate and a hydroxy group is also preferred.

In the invention, a cationic ring-opening polymerizable compound having at least one cyclic ether group such as an epoxy group or an oxetane group in the molecule can be favorably used as a UV curable resin (polymerizable compound).

Examples of the cationic polymerizable compound include curable compounds containing a ring-opening polymerizable group, and among these, heterocyclic group-containing curable compounds are more preferred. Examples of such curable compounds include epoxy derivatives, oxetane derivatives, tetrahydrofuran derivatives, cyclic lactone derivatives, cyclic carbonate derivatives, cyclic imino ethers such as oxazoline derivatives, and vinyl ethers, and among these, epoxy derivatives, oxetane derivatives, and vinyl ethers are preferred.

Preferred examples of the epoxy derivatives include monofunctional glycidyl ethers, polyfunctional glycidyl ethers, monofunctional alicyclic epoxies, and polyfunctional alicyclic epoxies.

Specific examples of compounds of the glycidyl ethers include diglycidyl ethers, (for example, ethylene glycol diglycidyl ether, bisphenol A diglycidyl ether, etc.), trifunctional or higher functional glycidyl ethers (for example, trimethylolethane triglycidyl ether, trimethylolpropane triglycidyl ether, glycerol triglycidyl ether, triglycidyl trishydroxyethyl isocyanurate, etc.), tetrafunctional or higher functional glycidyl ethers (for example, sorbitol tetraglycidyl ether, pentaerythritol tetraglycidyl ether, polyglycidyl ethers of cresol novolac resins, polyglycidyl ethers of phenolnovolac resins, etc.), alicyclic epoxies, polycyclohexyl epoxy methyl ethers of phenol novolac resins, etc.), and oxetanes.

As the polymerizable compound, an alicyclic epoxy derivative can be preferably used. An "alicyclic epoxy group" refers to a partial structure in which a double bond of a cycloalkene ring of a cyclopentene group, a cyclohexene group, or the like is epoxidized with a suitable oxidizing agent such as hydrogen peroxide or a peroxy acid.

As the alicyclic epoxy compound, a polyfunctional alicyclic epoxy compound having two or more cyclohexene oxide groups or cyclopentene oxide groups in one molecule is preferred. Specific examples of the alicyclic epoxy compound include 4-vinylcyclohexene dioxide, (3,4-epoxycyclohexyl)methyl-3,4-epoxycyclohexyl carboxylate, di(3,4-epoxycyclohexyl) adipate, di(3,4-epoxycyclohexylmethyl) adipate, bis(2,3-epoxycyclopentyl) ether, di(2,3-epoxy-6-methylcyclohexylmethyl) adipate, and dicyclopentadiene dioxide.

A normal glycidyl compound having an epoxy group but having no alicyclic structure in the molecule can be used alone or can also be used in combination with the above-mentioned alicyclic epoxy compound.

Examples of such a normal glycidyl compound include a glycidyl ether compound and a glycidyl ester compound, but it is preferred to use a glycidyl ether compound in combination.

Specific examples of the glycidyl ether compound include aromatic glycidyl ether compounds such as 1,3-bis(2,3-epoxypropyloxy)benzene, a bisphenol A type epoxy resin, a bisphenol F type epoxy resin, a phenol novolac type epoxy resin, a cresol novolac type epoxy resin, and a trisphenol methane type epoxy resin; and aliphatic glycidyl ether compounds such as 1,4-butanediol glycidyl ether, glycerol triglycidyl ether, propylene glycol diglycidyl ether, and trimethylolpropane tritriglycidyl ether. Examples of the glycidyl ester include glycidyl esters of linoleic acid dimers.

As the polymerizable compound, a compound having an oxetanyl group, which is a four-membered cyclic ether (hereinafter also simply referred to as "oxetane compound"), can be used. The oxetanyl group-containing compound is a compound having one or more oxetanyl groups in one molecule.

As the polymerization initiator, for example, azobisisobutyronitrile (AIBN), bis(2,4,6-trimethylbenzoyl)-phenylphosphine oxide, 2,4,6-trimethylbenzoyl-diphenyl-phosphine oxide, or the like can be used.

The second composition preferably does not contain a liquid component other than the liquid crystalline compound.

According to this, in the production process for the shaped article, it is not necessary to perform a treatment of removing the liquid component from the second composition, and thus, the productivity of the shaped article can be made more excellent. Further, shrinkage accompanying the removal of the liquid component can be prevented, and thus, the dimensional accuracy of the shaped article can be made more excellent.

The second composition may be any as long as it has fluidity when producing the shaped article, and may be, for example, a composition which does not have fluidity (in the form of a solid) when it is stored. Even in such a case, the composition can be generally made to have sufficient fluidity by heating or the like when producing the shaped article.

The viscosity of the second composition when producing the shaped article (for example, in the case where the second composition is ejected by an inkjet method, the viscosity when ejecting the second composition) is preferably 2 mPa·s or more and 30 mPa·s or less, more preferably 5 mPa·s or more and 20 mPa·s or less.

According to this, the ejection stability of the second composition by, for example, an inkjet method can be made more excellent.

The "viscosity" as used herein refers to a value obtained by measurement using an E-type viscometer (for example, VISCONIC ELD, manufactured by Tokyo Keiki, Inc., or the like).

Incidentally, in the production of the shaped article, a plurality of types of second compositions may be used.

For example, a second composition as an ink (color ink) which contains a coloring agent and a second composition as an ink (clear ink) which does not contain a coloring agent may be used. According to this, for example, as the second composition to be applied to a region which has an effect on the color tone in appearance of the shaped article, the second composition which contains a coloring agent is used, and as the second composition to be applied to a region which does not have an effect on the color tone in appearance of the shaped article, the second composition which does not contain a coloring agent can be used.

In addition, for example, a plurality of types of second compositions which contain a coloring agent having a different composition may be used. According to this, by using these second compositions in combination, an expressible color reproduction range can be expanded.

In the case where a plurality of types of second compositions (inks) are used, it is preferred to use at least a cyan ink, a magenta ink, and a yellow ink. According to this, by using these second compositions (inks) in combination, an expressible color reproduction range can be further expanded.

Further, for example, by using a plurality of types of second compositions having different types or contents of the liquid crystalline compound, the properties such as rigidity and elasticity required for the respective regions of the shaped article can be favorably adjusted.

Other Composition (Third Composition)

The composition set according to the invention may be any as long as it includes at least one type of first composition and at least one type of second composition, and may further include at least one type of composition (third composition) other than these compositions.

Shaped Article

Next, the shaped article (three-dimensional shaped article) according to the invention will be described.

The shaped article according to the invention is produced using the composition set according to the invention as described above.

According to this, the shaped article which contains a cellulosic material and has excellent strength and the like can be provided.

In particular, the shaped article according to the invention can be favorably produced using a production method described in detail later.

According to this, the shaped article which contains a cellulosic material and has excellent strength and the like can be efficiently produced.

The shaped article according to the invention has such excellent characteristics, and therefore can be applied to various uses.

The use of the shaped article according to the invention is not particularly limited, however, examples of the use include ornaments and exhibits such as dolls and figures; medical devices such as artificial dialyzers, implants, and stents; printing papers; optical members such as lenses (including variable focus lenses), phase difference films, and polarizing plates; gel materials such as culture scaffold materials to be used for cultivation of various cells, various bacteria, etc.; vehicles such as bicycles; nursing care goods such as wheelchairs, and the like, and constituent components thereof, and the like.

Among these, a stent is held in a state of being inserted into the body for a long period of time, and is required to have excellent strength, durability, biocompatibility, and the like. However, according to the invention, these requirements can be satisfied. Accordingly, when the invention is applied to a stent, the effect of the invention can be more remarkably exhibited. In particular, a stent to be applied to the blood vessel is repeatedly subjected to a large pressure change over a long period of time, and also has a greater influence on life and health when a defect occurs among various types of stents, and therefore is required to have more excellent strength, durability, and safety. However, according to the invention, these requirements can be satisfied.

Further, the shaped article according to the invention may be applied to any of prototypes, mass-produced products, and custom-made products.

Shaped Article Production Method

Next, a shaped article production method according to the invention will be described.

The shaped article according to the invention may be any as long as it is produced using the composition set according to the invention as described above, and the production method for the shaped article is not particularly limited.

Examples of the shaped article production method according to the invention include a method including bringing the first composition and the second composition in a liquid state into contact with each other, and allowing a chemical reaction involving the reactive functional group of the liquid crystalline compound to proceed.

According to this, a shaped article production method capable of efficiently producing a shaped article which contains a cellulosic material and has excellent strength and the like can be provided.

In particular, as the shaped article production method according to the invention, a method for producing a three-dimensional shaped article (a three-dimensional shaping method) by performing a layer forming step of forming a layer a plurality of times and stacking the layers on one another can be used.

According to this, even a shaped article required to have high dimensional accuracy or a shaped article having a complicated shape can be efficiently produced with sufficient dimensional accuracy. Further, the production method can be favorably applied also to the production of a plurality of types of shaped articles having different shapes and sizes.

Hereinafter, as a specific example of the shaped article production method, a case where a three-dimensional shaping method is applied, particularly, a case where the cellulose derivative is contained as particles in the first composition will be described.

FIGS. 1A to 1H are cross-sectional views schematically showing respective steps in a preferred embodiment of the shaped article production method according to the invention.

As shown in FIGS. 1A to 1H, the production method of this embodiment is configured as follows. The method includes a layer forming step (FIGS. 1A and 1D) in which a layer P1 having a given thickness is formed in a region surrounded by a side surface support part (frame body) 45 using a first composition (layer forming composition or particle-containing composition) P1' containing particles constituted by a material containing a cellulose derivative having a liquid crystalline functional group as described above, a second composition application step (FIGS. 1B and 1E) in which a second composition (ink) P12 which is in the form of a liquid and contains a liquid crystalline compound having a reactive functional group as described above is applied to the layer P1 by an inkjet method, and a solidification step (curing step) (FIGS. 1C and 1F) in which the second composition P12 applied to the layer P1 is solidified (cured) by a chemical reaction involving the liquid crystalline compound. These steps are sequentially and repeatedly performed (FIG. 1G), and thereafter, the method further includes an unbound particle removal step (FIG. 1H) in which among the particles constituting the respective layers P1, the particles which are not bound to one another (unnecessary part) by the solidified material (cured material) of the second composition P12 are removed.

Hereinafter, the respective steps will be described.

Layer Forming Step

Figure 1B:
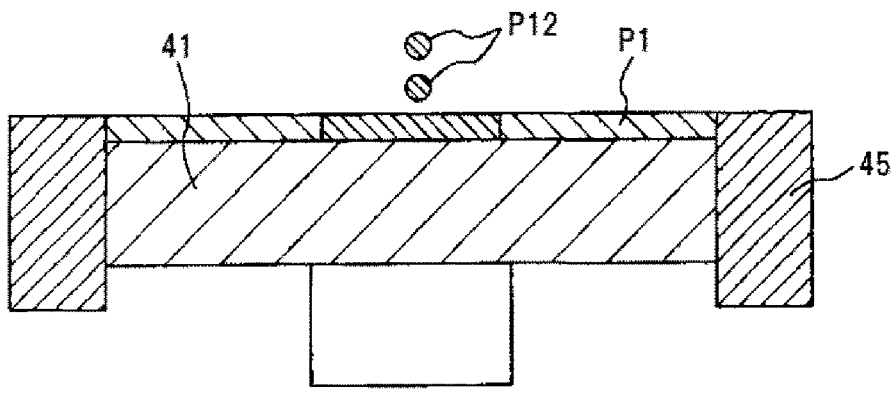
Figure 1C:
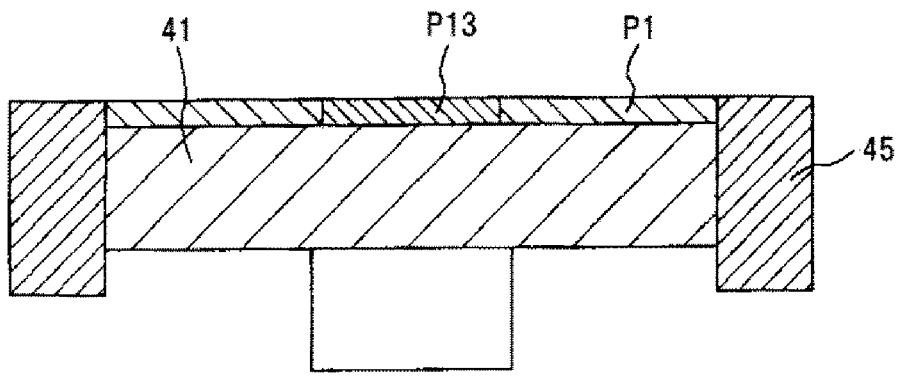
Figure 1D:
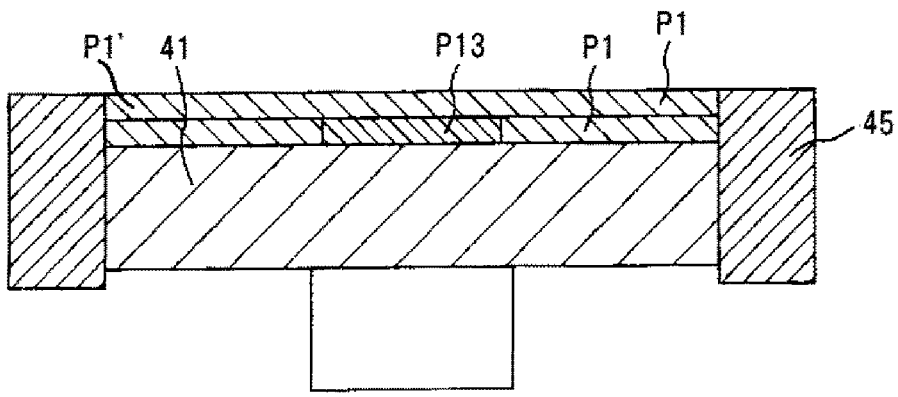

In the layer forming step, a layer P1 having a given thickness is formed using a first composition P1' containing particles constituted by a material containing a cellulose derivative having a liquid crystalline functional group (FIGS. 1A and 1D).

In this manner, by using the first composition containing particles P1', the dimensional accuracy of a shaped article (three-dimensional shaped article) P10 to be obtained finally can be made excellent. Further, the heat resistance, mechanical strength, and the like of the shaped article P10 can be made more excellent. In particular, the first composition P1' contains, as the particles, particles constituted by a material containing a cellulose derivative having a liquid crystalline functional group, and therefore, due to the effect of alignment, the mechanical strength of the shaped article P10 can be made more excellent.

In this step, by using a flattening unit, the layer P1 is formed such that the surface is flattened.

In the first layer forming step, the layer P1 is formed to a given thickness on the surface of a stage 41 (FIG. 1A). At this time, the side surface of the stage 41 and the side surface support part 45 are in a close contact (abutment) state, so that the first composition P1' is prevented from falling between the stage 41 and the side surface support part 45.

In each layer forming step after the first layer forming step, a new layer P1 (second layer) is formed on the surface of the layer P1 (first layer) formed in the previous step (FIG. 1D). At this time, the side surface of the layer P1 on the stage 41 (in the case where a plurality of layers P1 are present on the stage 41, at least the layer P1 provided on the uppermost side) and the side surface support part 45 are in a close contact (abutment) state, so that the first composition P1' is prevented from falling between the stage 41 and the layer P1 on the stage 41.

The first composition P1' may be applied onto a member having been subjected to an alignment treatment. That is, the stage 41 may have a surface having been subjected to an alignment treatment.

According to this, the liquid crystalline functional group of the cellulose derivative contained in the first composition P1' can be more favorably aligned, and thus, the mechanical strength, durability, reliability, and the like of the shaped article P10 to be obtained finally can be made more excellent.

Also each layer P1 formed after forming the first layer P1 is affected by the alignment state (the alignment state of the liquid crystalline functional group of the cellulose derivative and the liquid crystalline functional group of the liquid crystalline compound in a region to which the second composition P12 is applied) of the layer P1 on the lower side, and therefore, the liquid crystalline functional group of the cellulose derivative can be favorably aligned. That is, for each layer P1 formed after forming the first layer P1, the layer P1 on the lower side thereof functions as a member having been subjected to an alignment treatment.

As the alignment treatment, a method such as a rubbing treatment is favorably used.

Further, as a material of the surface of the stage 41, for example, a material such as polyimide for which an alignment treatment is favorably performed can be used.

In this step, the first composition P1' may be heated. By doing this, for example, in the case where the first composition P1' contains a molten component, the first composition P1' can be more favorably formed into a paste. Further, the cellulose derivative contained in the first composition P1' can be more favorably aligned.

In the case where a heating treatment is performed in this step, the heating temperature is preferably 30° C. or higher and 190° C. or lower, more preferably 35° C. or higher and 170° C. or lower.

According to this, the effect as described above can be more remarkably exhibited while sufficiently preventing undesirable denaturation, deterioration, or the like of the materials.

The heating treatment as described above may be performed, for example, after forming the layer P1 having a given thickness using the first composition P1'. Even in such a case, the same effect as described above is obtained. In the case where, for example, the first composition P1' contains a volatile liquid component, the heating treatment may be performed also as a heating treatment for volatilizing the liquid component.

The viscosity of the first composition P1' in this step is preferably 500 mPa·s or more and 1,000,000 mPa·s or less. According to this, the occurrence of an undesirable variation in the film thickness of the layer P1 to be formed can be more effectively prevented.

The thickness of the layer P1 to be formed in this step is not particularly limited, but is, for example, preferably 20 μm or more and 500 μm or less, more preferably 30 μm or more and 150 μm or less. According to this, while making the productivity of the shaped article P10 sufficiently excellent, the occurrence of undesirable irregularities or the like in the shaped article P10 to be produced is more effectively prevented, and the dimensional accuracy of the shaped article P10 can be made more excellent.

Second Composition Application Step (Ink Application Step)

Figure 1E:
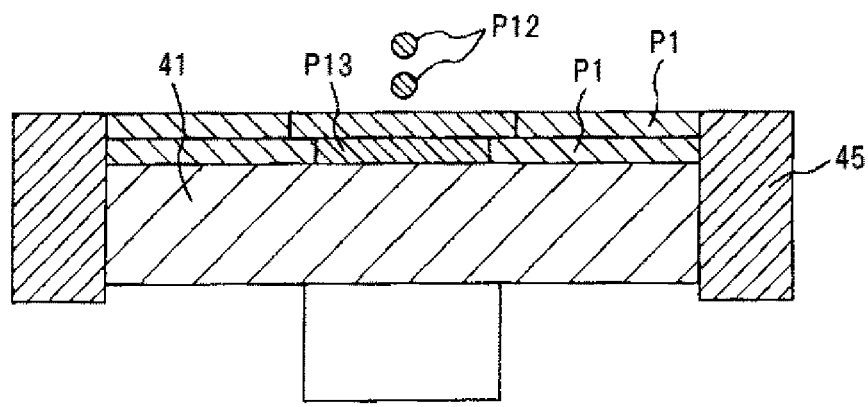

After the layer P1 is formed in the layer forming step, a second composition (ink) P12 which is in the form of a liquid and contains a liquid crystalline compound having a reactive functional group is applied to the layer P1 by an inkjet method (FIGS. 1B and 1E).

In this embodiment, the second composition P12 functions as a bonding solution (binding solution) for binding the particles constituting the layer P1.

The second composition P12 contains a liquid crystalline compound having a reactive functional group, and as described above, the affinity between the cellulose derivative contained in the layer P1 and the liquid crystalline compound contained in the second composition P12 is excellent. Due to this, the second composition P12 has excellent wettability to the particles constituting the layer P1, and therefore can favorably permeate into the voids between the particles constituting the layer P1, and also can sufficiently wet the surfaces of the particles. According to this, the adhesiveness between the solidified material (cured material) of the second composition P12 and the particles can be made excellent in the shaped article P10 to be obtained finally. Further, since both of the cellulose derivative and the liquid crystalline compound have a liquid crystalline functional group, the state of orientation thereof can be favorably aligned. Accordingly, the mechanical strength and the like of the shaped article P10 to be obtained finally can be made excellent.

In this step, the second composition P12 is selectively applied only to a region corresponding to a tangible part (a region where a tangible body is present) of the shaped article P10 to be produced in the layer P1.

By doing this, the particles constituting the layer P1 are bound to one another, whereby a bound part (tangible part) P13 having a desired shape can be formed in the end. In particular, the cellulose derivative constituting the particles and the liquid crystalline compound contained in the second composition P12 have excellent affinity, and therefore, repelling of the second composition P12 applied to the layer P1 or the like can be effectively prevented, and thus, the second composition P12 can be reliably applied in a desired shape and pattern. As a result, the dimensional accuracy of the shaped article P10 to be obtained finally can be made excellent.

This step may be performed while heating the second composition P12.

According to this, the fluidity of the second composition P12 can be made more favorable, so that the application pattern, the application amount, and the like of the second composition P12 can be more favorably adjusted, and thus, the dimensional accuracy and the like of the shaped article P10 to be obtained finally can be made more excellent. Further, the liquid crystalline compound contained in the second composition P12 and the cellulose derivative contained in the layer P1 to which the second composition P12 is applied can be more favorably aligned, and thus, the mechanical strength and the like of the shaped article P10 to be obtained finally can be made more excellent.

The temperature of the second composition P12 in this step is preferably 10° C. or higher and 100° C. or lower, more preferably 30° C. or higher and 95° C. or lower, further more preferably 35° C. or higher and 90° C. or lower.

According to this, the effect as described above can be more remarkably exhibited while sufficiently preventing undesirable denaturation, deterioration, or the like of the materials.

Further, in this step, a region to which the second composition P12 is to be applied (in this embodiment, the layer P1 to which the second composition P12 is applied) may be heated.

According to this, the application pattern, the application amount, and the like of the second composition P12 can be more favorably adjusted, and thus, the dimensional accuracy and the like of the shaped article P10 to be obtained finally can be made more excellent. Further, the permeability of the second composition P12 into the layer P1 can be made more excellent, and also the liquid crystalline compound and the cellulose derivative can be more favorably aligned, and thus, the mechanical strength of the shaped article P10 to be obtained finally can be made more excellent.

The temperature of the region to which the second composition P12 is to be applied in this step is preferably 10° C. or higher and 100° C. or lower, more preferably 30° C. or higher and 95° C. or lower, further more preferably 35° C. or higher and 90° C. or lower.

According to this, the effect as described above is more remarkably exhibited while sufficiently preventing undesirable denaturation, deterioration, or the like of the materials.

In this embodiment, the second composition P12 is applied by an inkjet method, and therefore, even if the application pattern of the second composition P12 has a finer shape, the second composition P12 can be applied with higher reproducibility. As a result, the dimensional accuracy of the shaped article P10 to be obtained finally can be further increased.

The second composition P12 may be applied onto a member having been subjected to an alignment treatment.

For example, the stage 41 may have a surface having been subjected to an alignment treatment, or the layer P1 to which the second composition P12 is applied has been previously subjected to a heating treatment as described above, and by doing this, the orientation of the liquid crystalline functional group of the cellulose derivative contained in the layer P1 may be aligned.

According to this, the liquid crystalline functional group of the liquid crystalline compound contained in the second composition P12 can be more favorably aligned, and thus, the mechanical strength, durability, reliability, and the like of the shaped article P10 to be obtained finally can be made more excellent.

Solidification Step (Curing Step)

Figure 1F:
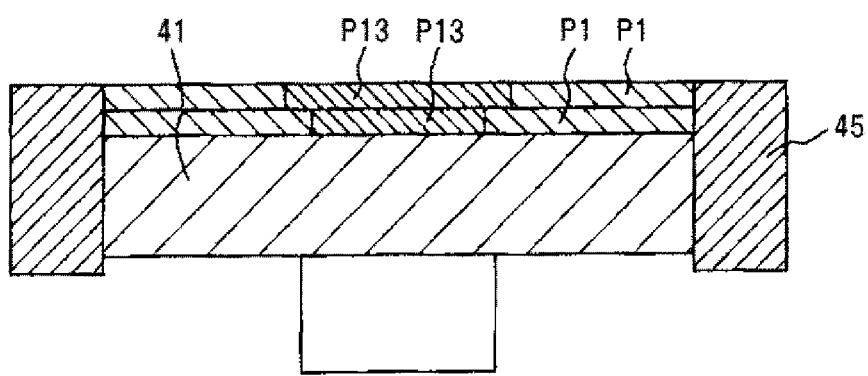
Figure 1G:
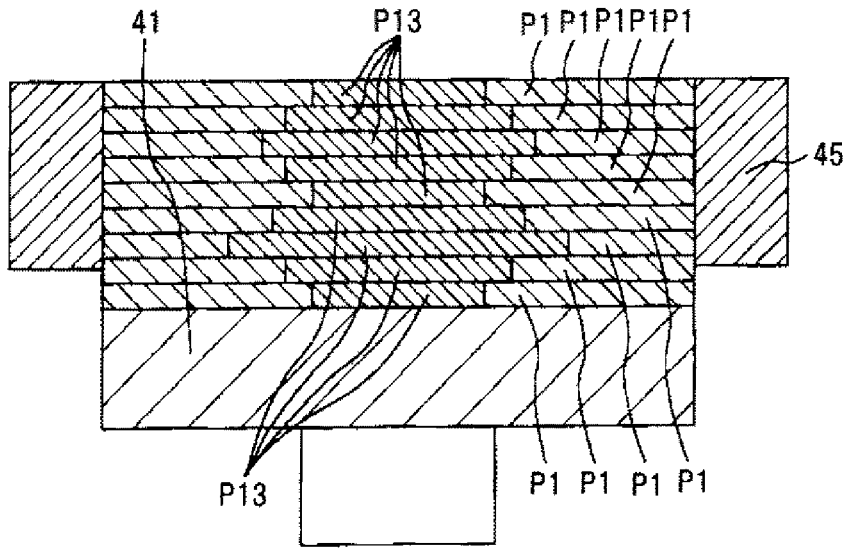
Figure 1H:
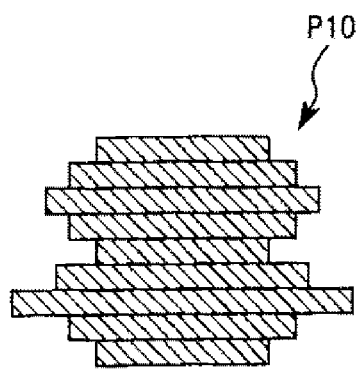

After the second composition P12 is applied to the layer P1 in the second composition application step (ink application step), the second composition P12 in the form of a liquid is solidified (cured), whereby a bound part (tangible part) P13 is formed (FIGS. 1C and 1F).

In this step, at least a chemical reaction (a chemical reaction to form a covalent bond) involving the reactive functional group of the liquid crystalline compound is performed. According to this, the hardness of the bound part (tangible part) P13 to be formed can be increased, and thus, the mechanical strength, durability, and reliability of the shaped article P10 to be obtained finally can be made excellent.

Further, in the case where the second composition P12 contains a cellulose derivative having a reactive functional group, a chemical reaction (a chemical reaction to form a covalent bond) involving the cellulose derivative may be performed. According to this, the hardness of the bound part (tangible part) P13 to be formed can be further increased, and thus, the mechanical strength, durability, and reliability of the shaped article P10 to be obtained finally can be made more excellent.

In this step, in the case where a chemical reaction (curing reaction) to form a covalent bond is performed, the chemical reaction can be performed by, for example, heating, irradiation with an energy ray (for example, a light such as a UV light, an electron beam, a positron beam, a neutron beam, an a beam, an ion beam, etc.), or the like.

In particular, in the case where the chemical reaction is allowed to proceed by heating, the structure of the production apparatus for the shaped article P10 can be simplified. Further, even if the raw material of the shaped article P10 is a material having a low light transmittance, a desired reaction can be allowed to favorably proceed.

In the case where the chemical reaction is allowed to proceed by heating, the heating temperature is preferably 85° C. or higher and 180° C. or lower, more preferably 90° C. or higher and 150° C. or lower.

Further, in the case where the chemical reaction is allowed to proceed by light irradiation, the productivity of the shaped article P10 can be made more excellent while more effectively preventing undesirable denaturation, deterioration, or the like of the materials.

In the case where the chemical reaction is allowed to proceed by light irradiation, as the light, for example, a UV light, an IR light, a visible light, an X-ray, a microwave, a radio wave, or the like can be used, however, it is preferred to use a UV light.

According to this, the productivity of the shaped article P10 can be made more excellent, and also the structure of the production apparatus for the shaped article P10 can be prevented from being complicated, and thus, the production cost of the shaped article P10 can be kept low.

Further, in the case where the chemical reaction is allowed to proceed by UV irradiation, the peak wavelength of the UV light is preferably 250 nm or more and 400 nm or less. Further, the UV irradiation time for each region to be cured is preferably 30 seconds or more and 60 seconds or less.

The second composition application step (ink application step) and the solidification step (curing step) may be performed concurrently. That is, before forming the entire pattern of the entire one layer P1, the reaction may be allowed to proceed sequentially from a region to which the second composition P12 is applied.

Unbound Particle Removal Step

After the steps as described above are performed repeatedly, as a post-treatment step, an unbound particle removal step (FIG. 1H) in which among the particles constituting the respective layers P1, the particles which are not bound to one another (unbound particles) by the solidified material (cured material) of the second composition P12 are removed is performed. By doing this, the shaped article P10 is taken out.

Examples of a specific method of this step include a method in which the unbound particles (unnecessary part) are removed by brushing with a brush or the like, a method in which the unbound particles (unnecessary part) are removed by suction, a method in which a gas such as air is blown, a method in which a liquid such as water is applied (for example, a method in which a stacked body obtained as described above is soaked in a liquid, a method in which a liquid is blown, etc.), and a method in which vibration such as ultrasonic vibration is applied. Further, two or more methods selected from these methods can be performed in combination. More specifically, a method in which a gas such as air is blown to the stacked body, and thereafter, the stacked body is soaked in a liquid such as water, a method in which ultrasonic vibration is applied to the stacked body while soaking the stacked body in a liquid such as water, and the like can be exemplified. Above all, it is preferred to adopt a method in which a liquid containing water is applied to the stacked body obtained as described above (particularly, a method in which the stacked body is soaked in a liquid containing water).

According to the production method according to the invention as described above, a shaped article which contains a cellulosic material and has excellent strength can be efficiently produced. Further, even a shaped article required to have high dimensional accuracy or a shaped article having a complicated shape can be efficiently produced with sufficient dimensional accuracy. Further, the production method can be favorably applied also to the production of a plurality of types of shaped articles having different shapes and sizes.

Shaped Article Production Apparatus

Next, a production apparatus (shaped article production apparatus) which can be used for producing the shaped article (three-dimensional shaped article) according to the invention will be described.

Figure 2:
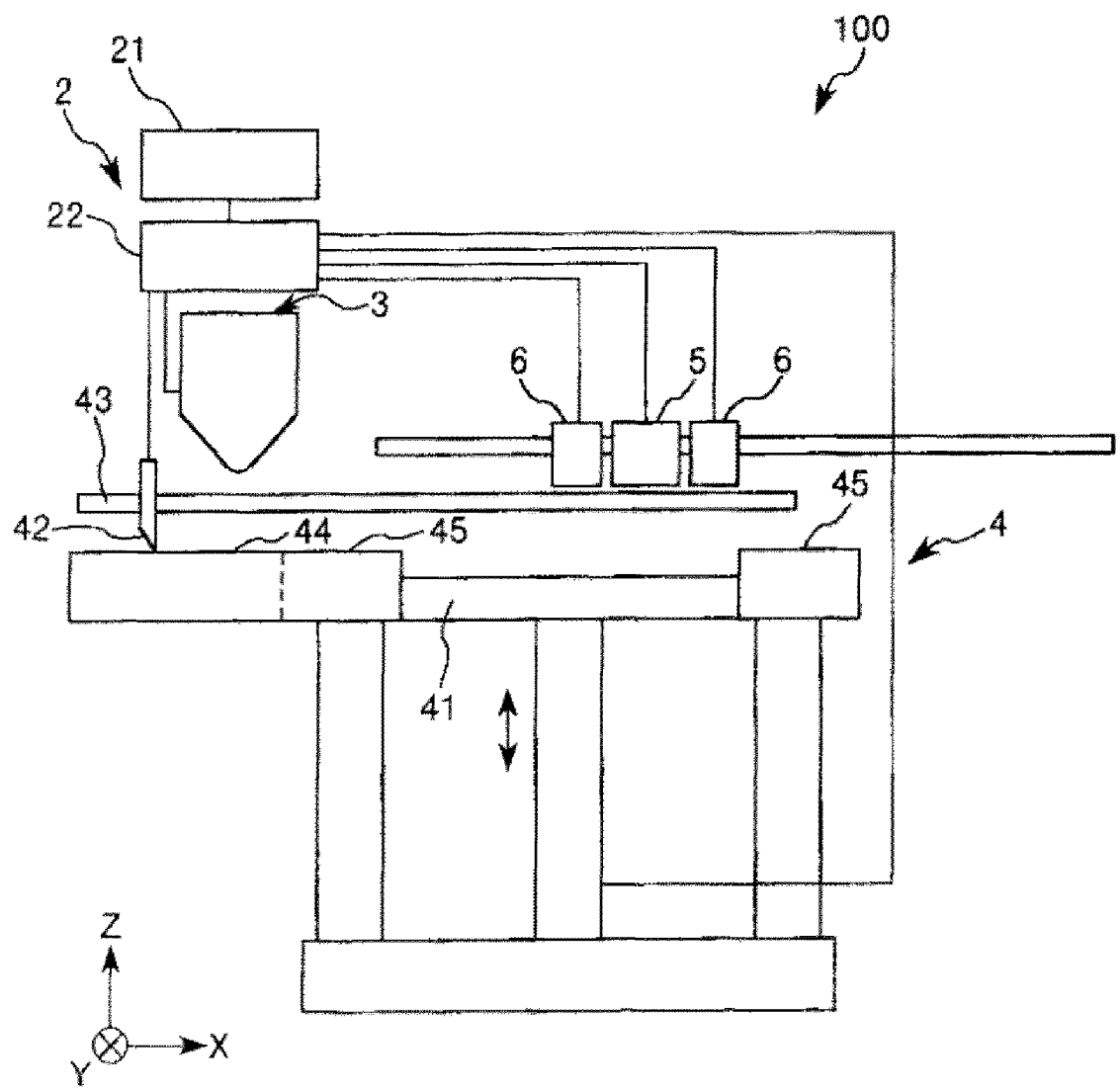
FIG. 2 is a cross-sectional view schematically showing a preferred embodiment of a production apparatus to be used for producing a shaped article according to the invention.

FIG. 2 is a cross-sectional view schematically showing a preferred embodiment of the production apparatus to be used for producing the shaped article according to the invention.

A shaped article production shown in FIG. 2 produces a shaped article P10 by repeatedly forming a layer P1 using a first composition containing particles (particle-containing composition) P1', and stacking the formed layers P1.

As shown in FIG. 2, the shaped article production apparatus 100 includes a control section 2, a first composition supply section (layer forming composition supply section or particle-containing composition supply section) 3 which supplies the first composition (layer forming composition or particle-containing composition) P1' containing particles constituted by a material containing a cellulose derivative having a liquid crystalline functional group as described above, a layer forming section 4 which forms the layer P1 using the first composition P1' supplied from the first composition supply section 3, a second composition ejection section (second composition application unit) 5 which ejects a second composition (ink) P12 in the form of a liquid to the layer P1, and an energy ray irradiation unit (solidification unit or bond forming unit) 6 which irradiates an energy ray for solidifying (curing) the second composition P12 in the form of a liquid.

The control section 2 includes a computer 21 and a drive control section 22.

The computer 21 is a common desk top computer or the like configured to include a CPU, a memory, etc. therein. The computer 21 digitizes the shape of the shaped article (three-dimensional shaped article) P10 as model data, and outputs cross-sectional data (slice data) obtained by slicing the shaped article P10 into a plurality of parallel layers of thin cross sections to the drive control section 22.

The drive control section 22 functions as a control unit for individually driving the layer forming section 4, the second composition ejection section 5, and the energy ray irradiation unit 6. Specifically, for example, the drive control section 22 controls the ejection pattern and the ejection amount of the second composition P12 in the form of a liquid by the second composition ejection section 5, the supply amount of the first composition P1' from the first composition supply section 3, the descent amount of a stage 41, and the like.

The first composition supply section 3 is configured to move under the command of the drive control section 22 and supply the first composition P1' held therein to a first composition temporary placing section 44.

The layer forming section 4 includes the first composition temporary placing section 44 which temporarily holds the first composition P1' supplied from the first composition supply section 3, a squeegee (flattening unit) 42 which forms the layer P1 while flattening the first composition P1' held by the first composition temporary placing section 44, a guide rail 43 which regulates the movement of the squeegee 42, the stage 41 which supports the formed layer P1, and a side surface support section (frame body) 45 which surrounds the stage 41.

When a new layer P1 is formed on a previously formed layer P1, the previously formed layer P1 is moved relatively downward with respect to the side surface support section 45. By doing this, the thickness of the layer P1 to be newly formed is defined.

In particular, in this embodiment, when a new layer P1 is formed on a previously formed layer P1, the stage 41 sequentially descends by a given amount under the command of the drive control section 22. In this manner, since the stage 41 is configured to be able to move in the Z-axis direction (vertical direction), the number of members to be moved for adjusting the thickness of the layer P1 when the new layer P1 is formed can be decreased, and therefore, the structure of the shaped article production apparatus 100 can be further simplified.

The stage 41 has a flat surface (a region to which the first composition P1' is applied).

According to this, the layer P1 having a highly uniform thickness can be easily and reliably formed. Further, in the shaped article P10 to be produced, the occurrence of undesirable deformation or the like can be effectively prevented.

The stage 41 is preferably constituted by a material with a high strength. Examples of the constituent material of the stage 41 include various metal materials such as stainless steel.

Further, the surface (the region to which the first composition P1' is applied) of the stage 41 may be subjected to a surface treatment. By doing this, for example, the adhesion of the constituent material of the first composition P1' or the constituent material of the second composition P12 to the stage 41 is more effectively prevented, or the durability of the stage 41 is made more excellent, and thus, the stable production of the shaped article P10 can be achieved for a longer period of time. Examples of a material to be used for the surface treatment of the surface of the stage 41 include fluororesins such as polytetrafluoroethylene. Further, for the stage 41, for example, a material such as polyimide subjected to an alignment treatment can be used. According to this, the effect as described above is obtained.

The squeegee 42 has an elongated shape extending in the Y-axis direction and includes a blade having a sharp edge shape at a lower tip end.

The length of the blade in the Y-axis direction is equal to or longer than the width (the length in the Y-axis direction) of the stage 41 (shaping region).

The shaped article production apparatus 100 may include a vibration mechanism (not shown) for giving small vibration to the blade so as to smoothly diffuse the first composition P1' with the squeegee 42.

The side surface support section 45 has a function to support the side surface of the layer P1 formed on the stage 41. The side surface support section 45 also has a function to define the area of the layer P1 when forming the layer P1.

Further, a surface (a region which can come in contact with the first composition P1') of the side surface support section 45 may be subjected to a surface treatment. By doing this, for example, the adhesion of the constituent material of the first composition P1' or the constituent material of the second composition P12 to the side surface support section 45 is more effectively prevented, or the durability of the side surface support section 45 is made more excellent, and thus, the stable production of the shaped article P10 can be achieved for a longer period of time. Further, when the previously formed layer P1 is moved relatively downward with respect to the side surface support section 45, the occurrence of an undesirable disturbance of the layer P1 can be effectively prevented. As a result, the dimensional accuracy and reliability of the shaped article P10 to be obtained finally can be made more excellent. Examples of a material to be used for the surface treatment of the surface of the side surface support section 45 include fluororesins such as polytetrafluoroethylene.

The second composition application unit (second composition ejection section) 5 applies the second composition P12 in the form of a liquid to the layer P1.

By including such a second composition application unit 5, the mechanical strength of the shaped article P10 can be easily and reliably made excellent.

In particular, in this embodiment, the second composition application unit 5 is a second composition ejection section which ejects the second composition P12 in the form of a liquid by an inkjet method.

According to this, the second composition P12 in the form of a liquid can be applied in a fine pattern, and even if the shaped article P10 has a fine structure, the shaped article P10 can be produced with higher productivity.

As a liquid droplet ejection system (a system of the inkjet method), a piezo system, a system for ejecting the second composition P12 in the form of a liquid by a bubble generated by heating the second composition P12 in the form of a liquid, or the like can be used, however, from the viewpoint that the constituent components of the second composition P12 are hardly denatured, and the like, a piezo system is preferred.

In the second composition ejection section (second composition application unit) 5, the pattern to be formed for each layer P1 and the amount of the second composition P12 to be applied to each part of the layer P1 are controlled by the command of the drive control section 22. The ejection pattern, the ejection amount, and the like of the second composition P12 using the second composition ejection section (second composition application unit) 5 are determined based on the slice data.

The energy ray irradiation unit (solidification unit or bond forming unit) 6 irradiates an energy ray for solidifying (curing) the second composition P12 in the form of a liquid applied to the layer P1.

In particular, in the configuration shown in the drawing, the energy ray irradiation unit (solidification unit or bond forming unit) 6 is provided on the upstream and downstream of the second composition ejection section (second composition application unit) 5 in a scanning direction.

According to this, the bond formation can be performed by the energy ray irradiation unit (solidification unit or bond forming unit) 6 on both forward and backward paths, and therefore, the productivity of the shaped article P10 can be made more excellent.

According to the shaped article production apparatus as described above, a shaped article which contains a cellulosic material and has excellent strength can be efficiently produced.

Hereinabove, preferred embodiments of the invention have been described, however, the invention is not limited thereto.

For example, in the above-mentioned embodiments, a case where a squeegee is used as the flattening unit has been mainly described, however, a roller or the like may be used in place of the squeegee.

Further, the production apparatus to be used for producing the shaped article according to the invention may include a recovery mechanism (not shown) for recovering the first composition which is not used for forming the layer in the first composition supplied from the first composition supply section. According to this, while preventing the accumulation of the excess first composition in a region where the layer is formed, a sufficient amount of the first composition can be supplied, and therefore, while more effectively preventing the occurrence of a defect in the layer, the shaped article can be produced more stably. Further, the recovered first composition can be used for producing the shaped article again, and therefore, this can contribute to the reduction in the production cost of the shaped article, so that this configuration is preferred also from the viewpoint of resource saving.

Further, the production apparatus to be used for producing the shaped article according to the invention may include a recovery mechanism for recovering the particles (first composition) removed in the unbound particle removal step.

Further, in the above-mentioned embodiments, a case where the tangible part is formed in all the layers has been described, however, a layer in which the tangible part is not formed may be formed. For example, the tangible part is not formed in a layer formed immediately above the stage, and the layer may be made to function as a sacrifice layer.

Further, in the above-mentioned embodiments, a case where the second composition application step is performed by an inkjet method has been mainly described, however, the second composition application step may be performed using another method (for example, another printing method).

Further, in the above-mentioned embodiments, a case where in addition to the layer forming step and the second composition application step (ink application step), the solidification step is also performed repeatedly along with the layer forming step and the ink application step has been described, however, the solidification step may not be performed repeatedly. For example, after forming a stacked body including a plurality of layers which have not been subjected to a solidification treatment for solidifying the second composition, the plurality of layers are subjected to the solidification treatment all together. According to this, for example, a treatment of applying an energy for solidifying (curing) the second composition can be reduced, and therefore, even in the case of using a material having low resistance to the energy in the production of the shaped article, undesirable denaturation, deterioration, or the like by application of the energy can be effectively prevented.

Further, in the above-mentioned embodiments, a case where a chemical reaction involving the reactive functional group of the liquid crystalline compound constituting the second composition is allowed to proceed after supplying the second composition to a given region has been described, however, the chemical reaction involving the reactive functional group of the liquid crystalline compound may be allowed to proceed partially before supplying the liquid crystalline compound to a given region.

In the invention, it is only necessary to use the first composition containing the cellulose derivative having a liquid crystalline functional group and the second composition containing the liquid crystalline compound having a reactive functional group for forming at least a portion of the tangible part of the shaped article, and the tangible part may have a portion which is formed without using the first composition and the second composition.

Further, in the production of the shaped article according to the invention, a pre-treatment step, an intermediate treatment step, or a post-treatment step may be performed as needed.

Examples of the pre-treatment step include a stage cleaning step.

As the intermediate treatment step, for example, in the case where the layer forming composition (first composition) is in the form of pellets, a step of stopping heating or the like (binder solidification step) may be included between the layer forming step and the second composition application step (ink application step). According to this, the binder constituting the pellets is formed into a solid state, and the layer can be obtained as a layer in which the binding force between the particles is higher. Further, for example, in the case where the layer forming composition (first composition) contains a solvent component (dispersion medium) such as water, a solvent component removal step in which the solvent component is removed may be included between the layer forming step and the second composition application step (ink application step). According to this, the layer forming step can be performed more smoothly, and an undesirable variation in the thickness of the layer to be formed can be more effectively prevented. As a result, the shaped article having higher dimensional accuracy can be produced with higher productivity.

Examples of the post-treatment step include a washing step, a shape adjustment step in which deburring or the like is performed, a coloring step, and a coating layer forming step.

Further, in the above-mentioned embodiments, a case where the flattening unit moves on the stage has been described, however, the flattening may be performed by moving the stage so as to change the positional relationship between the stage and the squeegee.

Further, the shaped article production apparatus may include, for example, a heating unit for heating the first composition and a heating unit for heating the second composition.

Further, in the above-mentioned embodiments, a case where the shaped article production apparatus includes an energy ray irradiation unit which irradiates an energy ray as the solidification unit has been representatively described, however, the solidification unit included in the shaped article production apparatus may be another unit such as a heating unit.

Further, the shaped article according to the invention may not be a shaped article produced using the above-mentioned method or apparatus.

Further, in the above-mentioned embodiments, a case where the first composition is used as a layer forming composition (particle-containing composition) and the second composition is used as an ink has been mainly described, however, for example, both of the first composition and the second composition may be used as an ink (for example, a liquid composition to be ejected by an inkjet method). In such a case, for example, the shaped article can be favorably produced by a three-dimensional shaping method by repeatedly performing a series of steps including allowing the chemical reaction involving the reactive functional group of the liquid crystalline compound to proceed after bringing the first composition ejected by an inkjet method and the second composition ejected by an inkjet method into contact with each other.

Further, in the above-mentioned embodiments, a case where the shaped article is produced using a three-dimensional shaping method (a method for producing a three-dimensional shaped article by performing a layer forming step of forming a layer a plurality of times and stacking the layers) has been mainly described, however, the shaped article may be produced using a method other than the three-dimensional shaping method.

Further, when the shaped article according to the invention is produced, a chemical reaction other than the above-mentioned chemical reaction may be performed. For example, in the case where the first composition contains a cellulose derivative having an acetylated hydroxy group, a reaction to release the acetyl group (deacetylation reaction) may be performed in the production of the shaped article. According to this, for example, in the first composition, while making the hydrophobicity of the cellulose derivative higher, the hydrophobicity of the shaped article to be obtained finally can be made relatively low, and thus, the properties of the shaped article can be made compatible with the productivity of the shaped article and the storage stability of the first composition.

EXAMPLES

Hereinafter, the invention will be described in more detail with reference to specific Examples, however, the invention is not limited only to these Examples. In the following description, a treatment in which the temperature condition is not particularly shown was performed at room temperature (25° C.). Further, for various measurement conditions in which the temperature condition is not particularly shown, values at room temperature (25° C.) are shown.

(1) Production of Three-Dimensional Shaped Article Example 1

1. Preparation of Composition Set 1-1. Preparation of First Composition (Layer Forming Composition)

Cellulose (10 g) was dissolved in a mixture of THF (200 mL) and pyridine (10 mL), and the resulting mixture was stirred well. To the mixture, a solution in which 2-bromo-2-methylpropionyl bromide (7 mL) was dissolved in THF (10 mL) was added dropwise at 0° C. over 1 hour. After completion of dropwise addition, the mixture was heated to 45° C. After heating the mixture for about 20 hours, the reaction mixture was added to a large amount of methanol. The deposited solid was filtered, dissolved in acetone, and then, reprecipitated in methanol. This procedure was repeated 3 times, and the obtained solid was dried in vacuo overnight, whereby a compound represented by the following formula (21) was obtained.

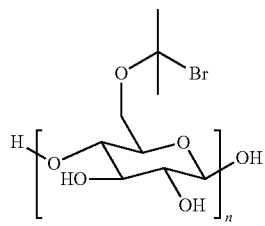

(21)

After the compound (1 g) represented by the above formula (21) was dissolved in N-methylpyrrolidone (NMP) (400 mL), allylamine (10 g) was added thereto, and thereafter, a compound (0.8 g) which has an ionic moiety and is represented by the following formula (22) was further added thereto.

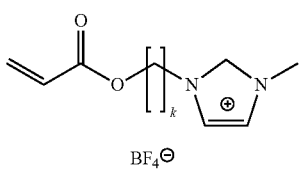

(22)

In the formula (22), k is 8.

Separately, a solution in which CuBr (0.13 g) and pentamethyldiethylenetriamine (PMDETA) (0.4 mL) were dissolved in NMP (15 mL) was prepared, and this solution was added to a solution containing the compound represented by the above formula (21) prepared as described above and the compound represented by the above formula (22), and the resulting mixture was heated and stirred at 75° C. for 12 hours.

In this manner, a compound represented by the following formula (23) was synthesized.

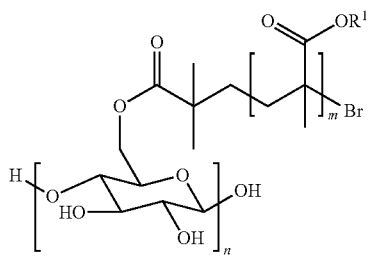

(23)

In the formula (23), $R^1$ is a substituent represented by the formula (9) in which k is 8 and $R^7$ is a methyl group.

Thereafter, to the above reaction mixture, a compound (a compound which is in the form of a liquid and has a liquid crystalline functional group) represented by the following formula (24) was added in an amount corresponding to a desired introduction amount, and the resulting mixture was heated and stirred at 75° C. for 12 hours.

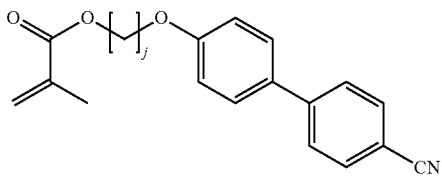

(24)

In the formula (24), j is 8.

Subsequently, to this reaction mixture, an NMP solution (10 mL) of tributyltin hydride (1 mL) was added, and the resulting mixture was further heated for 1 hour. Thereafter, the flask was uncapped, and oxygen was introduced into the flask to stop the reaction. The reaction mixture was diluted with 200 mL of acetone and passed through an alumina column to remove the catalyst. The resulting solution was added to 10 mass % hydrochloric acid, and the resulting solid was filtered, dissolved in acetone, reprecipitated in methanol, and then, dried in vacuo, whereby a cellulose derivative which has a liquid crystalline functional group and an ionic moiety as a chemical structure in common with an ionic liquid and is represented by the following formula (25) was obtained.

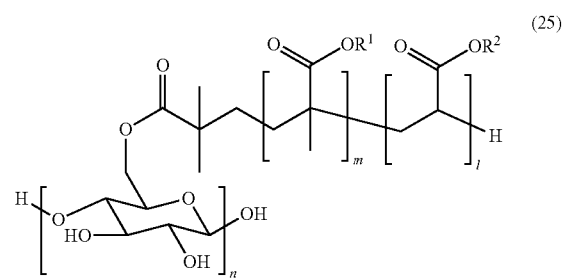

(25)

In the formula (25), $R^1$ is a substituent represented by the formula (9) in which k is 8 and $R^7$ is a methyl group. In the formula (25), $R^2$ is a substituent represented by the formula (10) in which j is 8.

The cellulose derivative obtained as described above had an average particle diameter of 2.6 μm.

The cellulose derivative represented by the above formula (25) obtained as described above in the form of particles (30.00% by mass), water (60.00% by mass), and ammonium polyacrylate (10.00% by mass) as a water-soluble resin were mixed, whereby a first composition (layer forming composition) was obtained.

In the first composition (layer forming composition), the cellulose derivative particles were in a favorable dispersed state.

1-2. Preparation of Second Composition (Ink)

The liquid crystalline compound (98 parts by mass) represented by the above formula (24) and bis(2,4,6-trimethylbenzoyl)phenylphosphine oxide (2 parts by mass) as a polymerization initiator were mixed, whereby a second composition (ink) was obtained.

2. Production of Three-Dimensional Shaped Article

Figure 3:
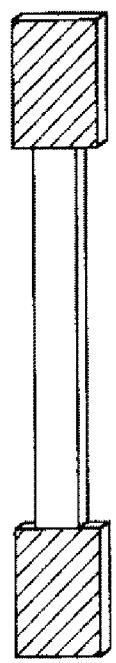
FIG. 3 is a perspective view showing the shape of a three-dimensional shaped article (three-dimensional shaped article A) produced in each of Examples and Comparative Examples.
Figure 4:
FIG. 4 is a perspective view showing the shape of a three-dimensional shaped article (three-dimensional shaped article B) produced in each of Examples and Comparative Examples.

By using a composition set including the first composition (layer forming composition) and the second composition (ink) obtained as described above, a three-dimensional shaped article A having a shape as shown in FIG. 3, that is, having a thickness of 4 mm and a length of 150 mm, and having regions, which are provided on both ends (on the upper and lower sides in the drawing), respectively, shown by the shaded portions, and each have a width of 20 mm and a length of 35 mm, and also having a region, which is sandwiched between these regions and has a width of 10 mm and a length of 80 mm, and a three-dimensional shaped article B having a shape as shown in FIG. 4, that is, having a rectangular parallelepiped shape with a thickness of 4 mm, a width of 10 mm, and a length of 80 mm were produced as follows.

First, a shaped article production apparatus as shown in FIG. 2 was prepared, and on the surface of the support body (stage), a layer having a thickness of 50 μm was formed by a squeegee method using the first composition (layer forming composition) (layer forming step). As the stage of the shaped article production apparatus, a stage having a surface constituted by polyimide subjected to an alignment treatment by a rubbing treatment was used.

Subsequently, after forming the layer, the layer was heated to 150° C. and left for 2 minutes, whereby water contained in the first composition (layer forming composition) was removed, and also the liquid crystalline functional group of the cellulose derivative was aligned.

Subsequently, to the layer from which water was removed, the second composition (ink) was applied in a given pattern by an inkjet method (second composition application step). In this step, the second composition (ink) previously heated to 85° C. or higher was ejected. Further, in this step, prior to the application of the second composition (ink), a region to which the second composition (ink) was to be applied was previously heated to 85° C. or higher.

Subsequently, the layer was irradiated with a UV light to allow a polymerization reaction (curing reaction) of the liquid crystalline compound contained in the layer to proceed, thereby curing the compound (solidification step).

Thereafter, a series of steps from the layer forming step to the curing step were performed repeatedly so as to stack a plurality of layers while changing the application pattern of the ink in accordance with the shape of a three-dimensional shaped article to be produced.

Thereafter, the stacked body obtained as described above was immersed in water, and ultrasonic vibration was applied thereto to remove the particles which were not bound to one another (unbound particles) by the solidified material (cured material) of the ink among the particles constituting the respective layers (unbound particle removal step). In this manner, two three-dimensional shaped articles A and two three-dimensional shaped articles B were obtained.

Examples 2 to 10

Composition sets (each set including a first composition and a second composition) and three-dimensional shaped articles were produced in the same manner as in the above Example 1 except that the types of raw materials to be used for the preparation of the first composition and the second composition, and the compositional ratios of the respective components were changed as shown in Table 1.

Comparative Example 1

A composition set and a three-dimensional shaped article were produced in the same manner as in the above Example 1 except that a compound represented by the following formula (34) was used as a compound which does not have a liquid crystalline functional group in place of the liquid crystalline compound.

(34)

Comparative Example 2

A composition set and a three-dimensional shaped article were produced in the same manner as in the above Example 1 except that a compound represented by the following formula (35) was used as a compound which does not have a reactive functional group in place of the liquid crystalline compound having a reactive functional group.

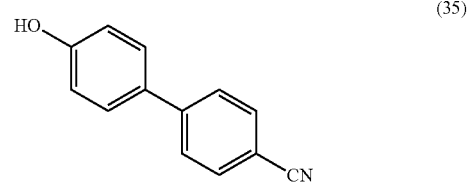 [SMILES: N#Cc1ccc(-c2ccc(O)cc2)cc1]

(35)

Comparative Example 3

A composition set and a three-dimensional shaped article were produced in the same manner as in the above Example 1 except that a compound represented by the following formula (30) which does not have a liquid crystalline functional group was used as the cellulose derivative.

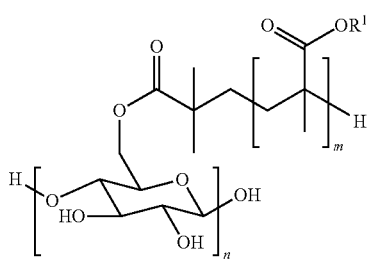

(30)

In the formula (30), $R^1$ is a substituent represented by the formula (9) in which k is 8 and $R^7$ is a methyl group.

Comparative Example 4

A composition set and a three-dimensional shaped article were produced in the same manner as in the above Example 1 except that cellulose was used in place of the cellulose derivative.

The formulations of the first compositions and the second compositions constituting the composition sets used in the above respective Examples and Comparative Examples are shown in Table 1. In the table, a compound which is a cellulose derivative represented by the above formula (25) in which $R^1$ is a substituent represented by the formula (9) in which k is 8 and $R^7$ is a methyl group, and $R^2$ is a substituent represented by the formula (10) in which j is 8 is denoted by "CD25A"; a compound which is a cellulose derivative represented by the above formula (25) in which $R^1$ is a substituent represented by the formula (9) in which k is 10 and $R^7$ is a methyl group, and $R^2$ is a substituent represented by the formula (11) in which j is 10 and $R^6$ is a butoxy group is denoted by "CD25B"; a compound which is a cellulose derivative represented by the following formula (26) in which $R^2$ is a substituent represented by the formula (10) in which j is 12 is denoted by "CD26A"; a compound which is a cellulose derivative represented by the following formula (26) in which $R^2$ is a substituent represented by the formula (11) in which j is 12 and $R^6$ is a butoxy group is denoted by "CD26B"; a compound which is a cellulose derivative represented by the above formula (30) in which $R^1$ is a substituent represented by the formula (9) in which k is 8 and $R^7$ is a methyl group is denoted by "CD30"; ammonium polyacrylate as a binder (water-soluble resin) is denoted by "PAA"; polyvinyl alcohol as a binder (water-soluble resin) is denoted by "PVA"; a compound which is a liquid crystalline compound represented by the above formula (24) in which j is 8 is denoted by "SLC24"; a compound which is a liquid crystalline compound represented by the following formula (31) in which j is 12 is denoted by "SLC31"; a compound represented by the above formula (34) is denoted by "C34"; a compound represented by the above formula (35) is denoted by "C35"; and bis(2,4,6-trimethylbenzoyl) phenylphosphine oxide is denoted by "I1". Further, in the above respective Examples, the viscosity of the ink (second composition) when the ink was ejected by an inkjet method was within the range of 5 mPa·s or more and 20 mPa·s or less in all cases. Further, in the above respective Examples, the temperature of the ink (second composition) when the ink was ejected was within the range of 35° C. or higher and 75° C. or lower in all cases. Further, in the above respective Examples, the temperature of the region to which the ink (second composition) was applied when the ink was ejected was previously adjusted within the range of 35° C. or higher and 75° C. or lower in all cases.

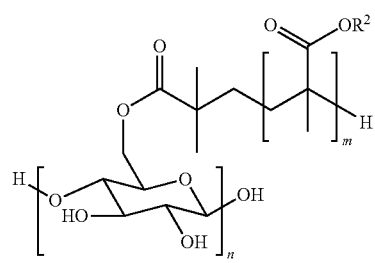

(26)

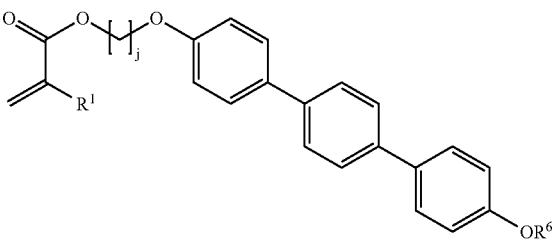

(31)

TABLE 1

| | First composition | | | | | | | | Second composition | | | | | |
|---|---|---|---|---|---|---|---|---|---|---|---|---|---|---|
| | Cellulose derivative | | Liquid component | | Binder | | Other component | | Liquid crystalline compound | | Polymerization initiator | | Other component | |
| | type | Content [parts by mass] | type | Content [parts by mass] | type | Content [parts by mass] | type | Content [parts by mass] | type | Content [parts by mass] | type | Content [parts by mass] | type | Content [parts by mass] |
| Example 1 | CD25A | 30 | water | 60 | PAA | 10 | — | — | SLC24 | 98 | I1 | 2 | — | — |
| Example 2 | CD26A | 30 | water | 60 | PAA | 10 | — | — | SLC24 | 98 | I1 | 2 | — | — |
| Example 3 | CD25B | 30 | water | 60 | PAA | 10 | — | — | SLC31 | 98 | I1 | 2 | — | — |
| Example 4 | CD26B | 30 | water | 60 | PAA | 10 | — | — | SLC31 | 98 | I1 | 2 | — | — |
| Example 5 | CD25A | 30 | water | 60 | PAA | 10 | — | — | SLC31 | 98 | I1 | 2 | — | — |
| Example 6 | CD26A | 30 | water | 60 | PAA | 10 | — | — | SLC31 | 98 | I1 | 2 | — | — |
| Example 7 | CD25B | 30 | water | 60 | PAA | 10 | — | — | SLC24 | 98 | I1 | 2 | — | — |
| Example 8 | CD25A | 35 | water | 55 | PVA | 10 | — | — | SLC24 | 98 | I1 | 2 | — | — |
| Example 9 | CD25B | 25 | water | 65 | PVA | 10 | — | — | SLC24 | 98 | I1 | 2 | — | — |
| Example 10 | CD25A | 40 | water | 50 | PVA | 10 | — | — | SLC24 | 98 | I1 | 2 | — | — |
| Comparative Example 1 | CD25A | 30 | water | 60 | PAA | 10 | — | — | — | — | I1 | 2 | C34 | 98 |

TABLE 1-continued

| | First composition | | | | | | | Second composition | | | | | |
|---|---|---|---|---|---|---|---|---|---|---|---|---|---|
| | Cellulose derivative | | Liquid component | | Binder | | Other component | | Liquid crystalline compound | | Polymerization initiator | | Other component | |
| | type | Content [parts by mass] | type | Content [parts by mass] | type | Content [parts by mass] | type | Content [parts by mass] | type | Content [parts by mass] | type | Content [parts by mass] | type | Content [parts by mass] |
| Comparative Example 2 | CD25A | 30 | water | 60 | PAA | 10 | — | — | — | — | I1 | 2 | C35 | 98 |
| Comparative Example 3 | — | — | water | 60 | PAA | 10 | CD30 | 30 | SLC24 | 98 | I1 | 2 | — | — |
| Comparative Example 4 | — | — | water | 60 | PAA | 10 | cellulose | 30 | SLC24 | 98 | I1 | 2 | — | — |

2 Evaluation 2.1 Dimensional Accuracy

With respect to the three-dimensional shaped articles B of the above respective Examples and Comparative Examples, the thickness, width, and length were measured, and the deviation amount from the set value was determined and evaluated according to the following criteria.

A: The deviation amount from the set value which is the largest of the deviation amounts from the set values for the thickness, width, and length is less than 1.0%.

B: The deviation amount from the set value which is the largest of the deviation amounts from the set values for the thickness, width, and length is 1.0% or more and less than 2.0%.

C: The deviation amount from the set value which is the largest of the deviation amounts from the set values for the thickness, width, and length is 2.0% or more and less than 4.0%.

D: The deviation amount from the set value which is the largest of the deviation amounts from the set values for the thickness, width, and length is 4.0% or more and less than 7.0%.

E: The deviation amount from the set value which is the largest of the deviation amounts from the set values for the thickness, width, and length is 7.0% or more.

2.2 Tensile Strength

With respect to the three-dimensional shaped articles A of the above respective Examples and Comparative Examples, the tensile strength was measured under the conditions that the tensile yield stress was 50 mm/min and the tensile modulus of elasticity was 1 ram/min according to JIS K 7161:1994 (ISO 527:1993) and evaluated according to the following criteria.

A: The tensile strength is 100 MPa or more.

B: The tensile strength is 10 MPa or more and less than 100 MPa.

C: The tensile strength is 1 MPa or more and less than 10 MPa.

D: The tensile strength is less than 1 MPa.

These results are summarized in Table 2.

TABLE 2

| | Dimensional accuracy | Tensile strength |
|---|---|---|
| Example 1 | A | A |
| Example 2 | A | A |
| Example 3 | B | B |
| Example 4 | B | B |
| Example 5 | B | B |
| Example 6 | B | C |
| Example 7 | B | C |
| Example 8 | A | A |
| Example 9 | B | B |
| Example 10 | B | B |
| Comparative Example 1 | E | D |
| Comparative Example 2 | E | D |
| Comparative Example 3 | E | D |
| Comparative Example 4 | E | D |

As apparent from Table 2, according to the invention, a three-dimensional shaped article having excellent mechanical strength and excellent dimensional accuracy could be obtained. On the other hand, in Comparative Examples, satisfactory results were not obtained.

What is claimed is:

1. A composition set comprising:

a first composition which contains a cellulose derivative having a liquid crystalline functional group comprising one or more of the following liquid crystalline functional groups:

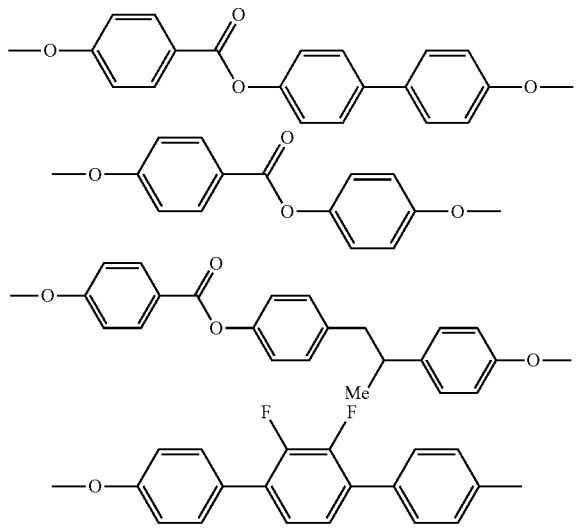

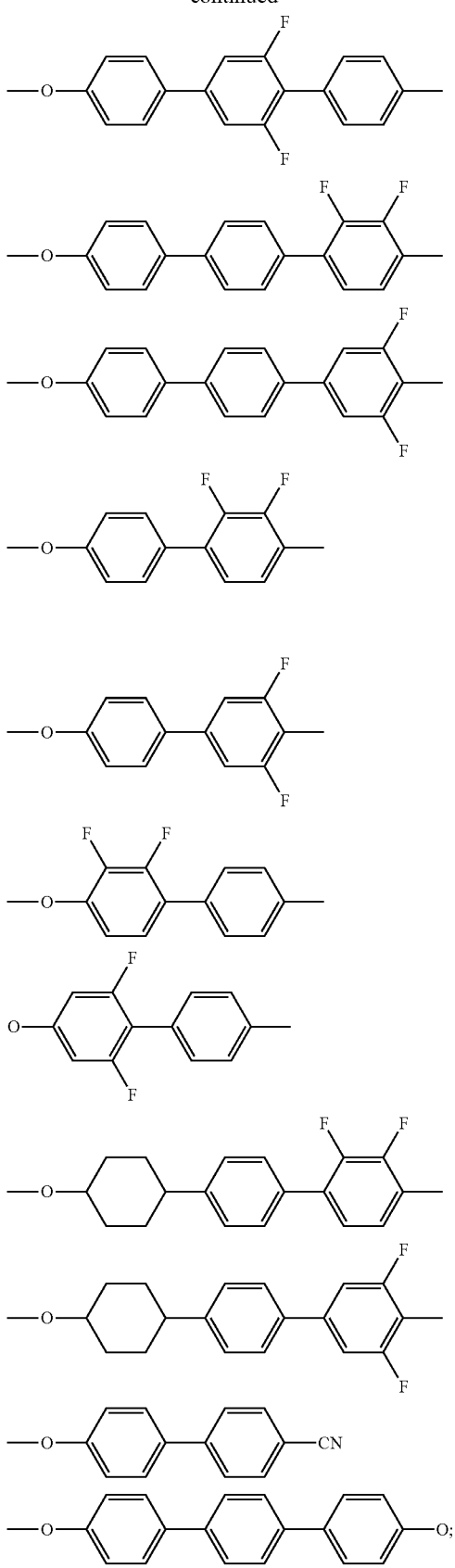

and
a second composition which contains a liquid crystalline compound having a reactive functional group, the reactive functional group comprising one or more of a carbon-carbon double bond, a vinyl group, a (meth)acryloyl group, a hydroxyl group, or a carboxyl group.

2. The composition set according to claim 1, wherein the first composition comprises particles, surfaces of the particles being formed from the cellulose derivative.

3. The composition set according to claim 2, wherein the first composition contains a liquid component which functions as a dispersion medium for dispersing the particles.

4. The composition set according to claim 2, wherein the particles have an average particle diameter of 1 µm or more and 25 µm or less.

5. The composition set according to claim 1, wherein the second composition does not contain a liquid component other than the liquid crystalline compound.

6. The composition set according to claim 1, wherein the reactive functional group contains a carbon-carbon double bond.

7. The composition set according to claim 6, wherein the reactive functional group is a (meth)acryloyl group.

8. The composition set according to claim 1, wherein the cellulose derivative includes the liquid crystalline functional group as a repeating unit of a polymer chain having a repeating structure.

9. The composition set according to claim 1, wherein the reactive functional group of the liquid crystalline compound is UV irradiation curable.

10. A shaped article, which is produced using the composition set according to claim 1.

11. A shaped article, which is produced using the composition set according to claim 2.

12. The composition set according to claim 1, wherein the second composition is in a liquid state.

13. The composition set according to claim 1, wherein the liquid crystalline functional group is located at $R^3$, in the following formula:

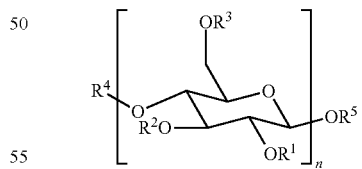

wherein $R^1$, $R^2$, $R^3$, $R^4$ and $R^5$ each independently represent a hydrogen atom or a substituent.

14. The A composition set according to claim 1, comprising:
a first composition which contains a cellulose derivative having a liquid crystalline functional group, wherein the cellulose derivative having the liquid crystalline functional group comprises at least one of the following chemical structures:

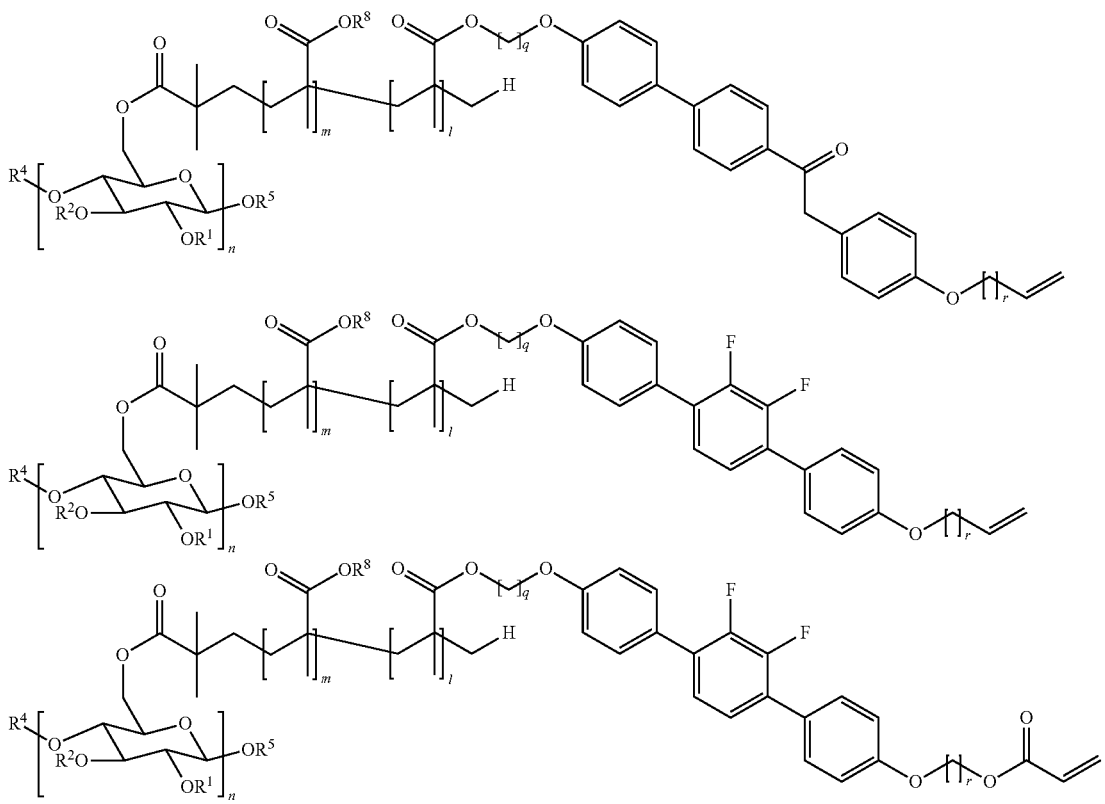

wherein l, m, and n are each independently an integer of 2 or more, q and r are each independently an integer of 1 or more, $R^1$, $R^2$, $R^4$ and $R^5$ each independently represent a hydrogen atom or a acetyl group, and $R^8$ is an ionic group; and a second composition which contains a liquid crystalline compound having a reactive functional group, the reactive functional group comprising one or more of a carbon-carbon double bond, a vinyl group, a (meth) acryloyl group, a hydroxyl group, or a carboxyl group.

15. The composition set according to claim 1, wherein the liquid crystalline functional group of the cellulose derivative comprises at least one of the formulae below:

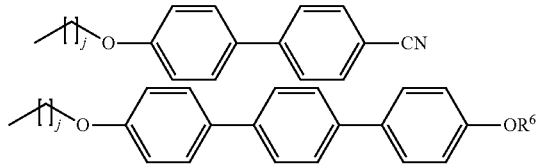

wherein j is an integer of 1 or more and $R^6$ is a hydrogen atom or an alkyl group.

16. The composition set according to claim 1, wherein a liquid crystalline functional group of the liquid crystalline compound is the same as the liquid crystalline functional group of the cellulose derivative.

* * * * *